United States Patent
Shimada

(10) Patent No.: US 9,713,552 B2
(45) Date of Patent: Jul. 25, 2017

(54) METHOD AND APPARATUS FOR PRODUCING WEARING ARTICLE, AND WEARING ARTICLE

(75) Inventor: Takahiro Shimada, Settsu (JP)

(73) Assignee: ZUIKO CORPORATION, Osaka (JP)

( * ) Notice: Subject to any disclaimer, the term of this patent is extended or adjusted under 35 U.S.C. 154(b) by 1050 days.

(21) Appl. No.: 13/820,770

(22) PCT Filed: Aug. 26, 2011

(86) PCT No.: PCT/JP2011/004768
§ 371 (c)(1),
(2), (4) Date: Mar. 5, 2013

(87) PCT Pub. No.: WO2012/032732
PCT Pub. Date: Mar. 15, 2012

(65) Prior Publication Data
US 2013/0160194 A1    Jun. 27, 2013

(30) Foreign Application Priority Data

Sep. 9, 2010    (JP) .................................. 2010-202132

(51) Int. Cl.
*A41B 9/00*    (2006.01)
*A61F 13/15*    (2006.01)
*A61F 13/49*    (2006.01)

(52) U.S. Cl.
CPC .......... *A61F 13/15699* (2013.01); *A41B 9/00* (2013.01); *A61F 13/15747* (2013.01);
(Continued)

(58) Field of Classification Search
CPC .......... A61F 13/15739; A61F 13/15747; A61F 2013/15878
See application file for complete search history.

(56) References Cited

U.S. PATENT DOCUMENTS 5,735,840 A * 4/1998 Kline ................ A61F 13/15699
604/385.23
6,022,432 A    2/2000 Elsberg et al.
(Continued)

FOREIGN PATENT DOCUMENTS

EP    0 320 989    6/1989
JP    2-140163    5/1990
(Continued)

OTHER PUBLICATIONS

International Search Report of Nov. 29, 2011.

*Primary Examiner* — Matthew Daniels
*Assistant Examiner* — Marta Dulko
(74) *Attorney, Agent, or Firm* — Gerald E. Hespos; Michael J. Porco; Matthew T. Hespos

(57) ABSTRACT

The method comprises the steps of: preparing a first suction-holding section and a second suction-holding section; positioning the first suction-holding section and the second suction-holding section in such a manner that respective surfaces of the first suction-holding section and the second suction-holding section are aligned side-by-side while facing the same side; suction-holding a forward surface of a main body of an developed module by the first suction-holding section, and suction-holding a rearward surface of the main body of the developed module by the second suction-holding section; closing the first suction-holding section and the second suction-holding section to fold the main body in half; and releasably joining superimposed portions of the developed module half-folded by the half-folding step.

7 Claims, 20 Drawing Sheets

(52) U.S. Cl.
CPC .. *A61F 13/15756* (2013.01); *A61F 13/15804* (2013.01); *A61F 13/49058* (2013.01)

(56) References Cited

U.S. PATENT DOCUMENTS

| | | | |
|---|---|---|---|
| 7,387,148 B2* | 6/2008 | Vogt | A61F 13/15756 156/475 |
| 2003/0125702 A1* | 7/2003 | Couture-Dorschner | A61F 13/15739 604/387 |
| 2006/0276320 A1 | 12/2006 | Aiolfi et al. | |
| 2007/0049890 A1* | 3/2007 | Popp | A61F 13/49004 604/385.11 |
| 2007/0137011 A1* | 6/2007 | Couillard | A61F 13/15772 28/100 |
| 2008/0083489 A1* | 4/2008 | Schneider | A61F 13/15739 156/258 |
| 2011/0118693 A1* | 5/2011 | Konishi | A61F 13/15747 604/391 |
| 2011/0287919 A1 | 11/2011 | Umebayashi | |
| 2011/0297294 A1* | 12/2011 | McCabe | A61F 13/15747 156/66 |
| 2011/0303351 A1 | 12/2011 | Nakakado | |
| 2011/0319243 A1* | 12/2011 | Fujita | A61F 13/15747 493/357 |
| 2012/0184937 A1* | 7/2012 | Sablone | A61F 13/62 604/385.24 |

FOREIGN PATENT DOCUMENTS

| | | |
|---|---|---|
| JP | 6-328600 | 11/1994 |
| JP | 7-205943 | 8/1995 |
| JP | 8-17792 | 2/1996 |
| JP | 2002-518097 | 6/2002 |
| JP | 2002-355270 | 12/2002 |
| JP | 2006-326313 | 12/2006 |
| JP | 2009-519744 | 5/2009 |
| WO | 2010/089964 | 8/2010 |
| WO | 2010/092935 | 8/2010 |

* cited by examiner

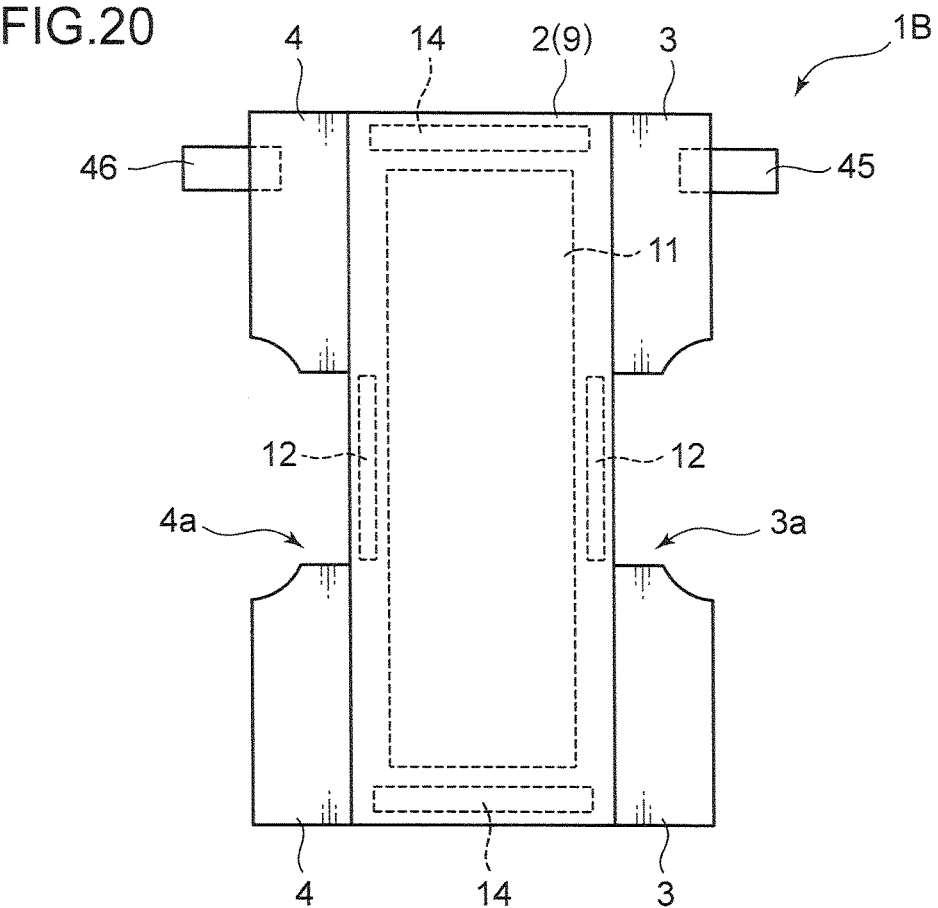
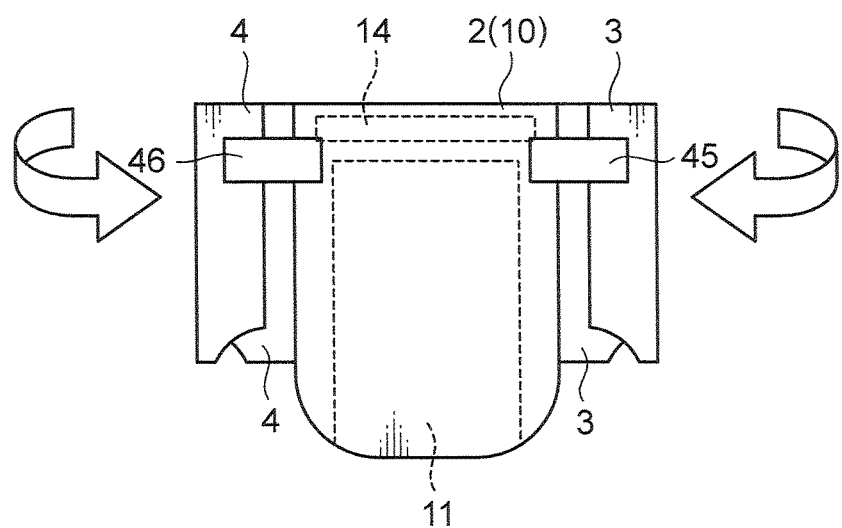

METHOD AND APPARATUS FOR PRODUCING WEARING ARTICLE, AND WEARING ARTICLE

TECHNICAL FIELD

The present invention relates to a method and apparatus for producing a wearing article.

BACKGROUND ART

Heretofore, there has been known a wearing article which comprises a main body adapted to extend from a front abdominal region to a rear dorsal region via a crotch region of a wearer, and a side panel for covering a lateral surface of a waist region of the wearer.

As this type of wearing article, an absorbent garment of Japanese Examined Patent Publication No. H08-017792B is known, for example. The absorbent garment of Japanese Examined Patent Publication No. H08-017792B comprises a waste containment section (main body) adapted to extend from a front abdominal region to a rear dorsal region via a crotch region of a wearer, and a side panel provided on each of laterally opposite sides of the waste containment section.

The absorbent garment of Japanese Examined Patent Publication No. H08-017792B is produced in the following manner. Firstly, an developed module is produced which comprises an absorbent assembly corresponding to the waste containment section, and four side panels a respective two of which extend from a respective one of front and rear end portions of the absorbent assembly, laterally in respective opposite directions. Then, the developed module is folded in half by pressing a tucker bar against a longitudinally central position of the absorbent assembly.

However, in the production method of Japanese Examined Patent Publication No. H08-017792B, in order to half-fold the absorbent assembly, a strong pressing force from the tucker bar is applied to only a portion of the absorbent assembly corresponding to a bend line. This is likely to cause damage to the absorbent assembly. Moreover, in the production method of Japanese Examined Patent Publication No. H08-017792B, the absorbent assembly, which encloses an absorbent body and an elastic member and thereby has a non-uniform thickness, is half-folded on the basis of the pressing position of the tucker bar. This also causes a problem that a folding line of the absorbent assembly becomes positionally unstable, resulting in poor accuracy of the half-folding.

Therefore, as an apparatus for accurately half-folding a workpiece while suppressing damage of the workpiece, a folding apparatus of the following Japanese Unexamined Patent Publication No. H07-205943A is known, for example. FIGS. 26 to 28 are schematic diagrams of a folding operation using the folding apparatus of Japanese Unexamined Patent Publication No. H07-205943A.

As illustrated in FIG. 26, the folding apparatus of Japanese Unexamined Patent Publication No. H07-205943A comprises a suction-holding section 102 for sucking and holding one of two regions of a workpiece 101, and a suction-holding section 103 for sucking and holding the other region of the workpiece 101. The suction-holding sections 102, 103 are adapted to be relatively displaceable between a state illustrated in FIG. 26, in which the first suction-holding section 102 and the second suction-holding section 103 are opened, and a state illustrated in FIG. 27, in which the first suction-holding section 102 and the second suction-holding section 103 are closed. Thus, the folding apparatus of Japanese Unexamined Patent Publication No. H07-205943A is operable to close the suction-holding section 102 holding one of the two regions of the workpiece 101 to be folded in half, and the suction-holding section 103 holding the other region, to thereby half-fold the workpiece 101. Then, the folding apparatus of Japanese Unexamined Patent Publication No. H07-205943A is operable, after half-folding the workpiece 101, to re-open the suction-holding sections 102, 103 as illustrated in FIG. 28, and transfer the half-folded workpiece 101 to a transfer conveyer located downstream of the folding apparatus, while sucking and holding the half-folded workpiece 101 by one 102 of the suction-holding sections.

However, the folding apparatus of Japanese Unexamined Patent Publication No. H07-205943A has a problem that a folded position of the workpiece 101 is undesirably displaced after the half-folding operation. More specifically, the folding apparatus of Japanese Unexamined Patent Publication No. H07-205943A can apply a suction-holding force from the suction-holding section 102 directly to the one region of the half-folded workpiece 101, as illustrated in FIG. 28. On the other hand, it is impossible to sufficiently apply the suction-holding force from the suction-holding section 102 to the other region of the half-folded workpiece 101, because the other region is located on a side opposite to the suction-holding section 102 across the one region.

Thus, the folding apparatus of Japanese Unexamined Patent Publication No. H07-205943A has difficulty in reliably maintaining the folded position of the workpiece 101 after the half-folding operation.

SUMMARY OF THE INVENTION

It is an object of the present invention to provide a method and apparatus, for producing a wearing article, capable of accurately folding a main body in half while suppressing damage of the main body, and maintaining a folded position of the main body after the half-folding step, and a wearing article produced thereby.

In order to solve the above problems, the present invention provides a method for producing a wearing article which comprises a main body adapted to extend from a front abdominal region to a rear dorsal region via a crotch region of a wearer, and a side panel for covering a lateral surface of a waist region of the wearer. The method comprises: an developed module preparing step of preparing an developed module which comprises the main body, and at least two side panel segments extending from at least one of front and rear end portions of the main body, laterally in respective opposite directions; a suction-holding section preparing step of preparing a first suction-holding section having a first suction-holding surface capable of suction-holding a forward surface of the main body in the developed module, and a second suction-holding section having a second suction-holding surface capable of suction-holding a rearward surface of the main body in the developed module; a suction-holding section positioning step of positioning the first suction-holding section and the second suction-holding section in such a manner that the first suction-holding surface and the second suction-holding surface are aligned side-by-side while facing a same side; a suction-holding step of, after the suction-holding section positioning step, suction-holding the forward surface of the main body in the developed module by the first suction-holding surface, and suction-holding the rearward surface of the main body in the developed module by the second suction-holding surface; a half-folding step of, after the suction-holding step, closing the first suction-holding section and the second suction-holding section in such a manner that the first suction-holding surface and the second suction-holding surface are located in opposed relation to each other, thereby folding the main body in half; and a temporarily joining step of externally heating and/or pressing superimposed portions of the developed module half-folded by the half-folding step, thereby releasably joining the superimposed portions of the developed module.

The present invention also provides an apparatus for producing a wearing article using an developed module which comprises a main body, and at least two side panel segments extending from at least one of front and rear end portions of the main body, laterally in respective opposite directions, wherein the wearing article is capable of being worn in a state in which the main body extends from a front abdominal region to a rear dorsal region via a crotch region of a wearer, and the side panel segments cover a lateral surface of a waist region of the wearer. The apparatus comprises: a first suction-holding section having a first suction-holding surface capable of suction-holding a forward surface of the main body in the developed module; a second suction-holding section having a second suction-holding surface capable of suction-holding a rearward surface of the main body in the developed module; a support member supporting the first suction-holding section and the second suction-holding section in such a manner that they are relatively displaceable between an open position where the first suction-holding surface and the second suction-holding surface are aligned side-by-side while facing a same side, and a closed position where the first suction-holding surface and the second suction-holding surface are located in opposed relation to each other; and a temporarily joining portion provided in at least one of the first suction-holding section and the second suction-holding section, and adapted to externally heat and/or press superimposed portions of the developed module half-folded between the first and second suction-holding surfaces at the closed position, thereby releasably joining the superimposed portions together.

Further, the present invention provides a wearing article including an developed module which comprises a main body and at least two side panel segments extending from at least one of front and rear end portions of the main body, laterally in respectively opposite directions, wherein the main body is folded in half, the wearing article comprising a temporarily jointed area where superimposed portions of the developed module are releasably joined together.

The present invention makes it possible to accurately fold the main body in half while suppressing damage of the main body, and maintain a folded position of the main body after the half-folding step.

BRIEF DESCRIPTION OF THE DRAWINGS

FIG. 20 is a development diagram illustrating a general configuration of a disposable diaper according to a second embodiment of the present invention.

FIG. 21 is a front view illustrating a wearing or use state of the disposable diaper in FIG. 20.

DESCRIPTION OF EMBODIMENTS

With reference to the accompanying drawings, an embodiment of the present invention will now be described. It should be understood that the following embodiment is a specific example of the present invention, and is not intended to restrict a technical scope of the present invention.

Figure 1:
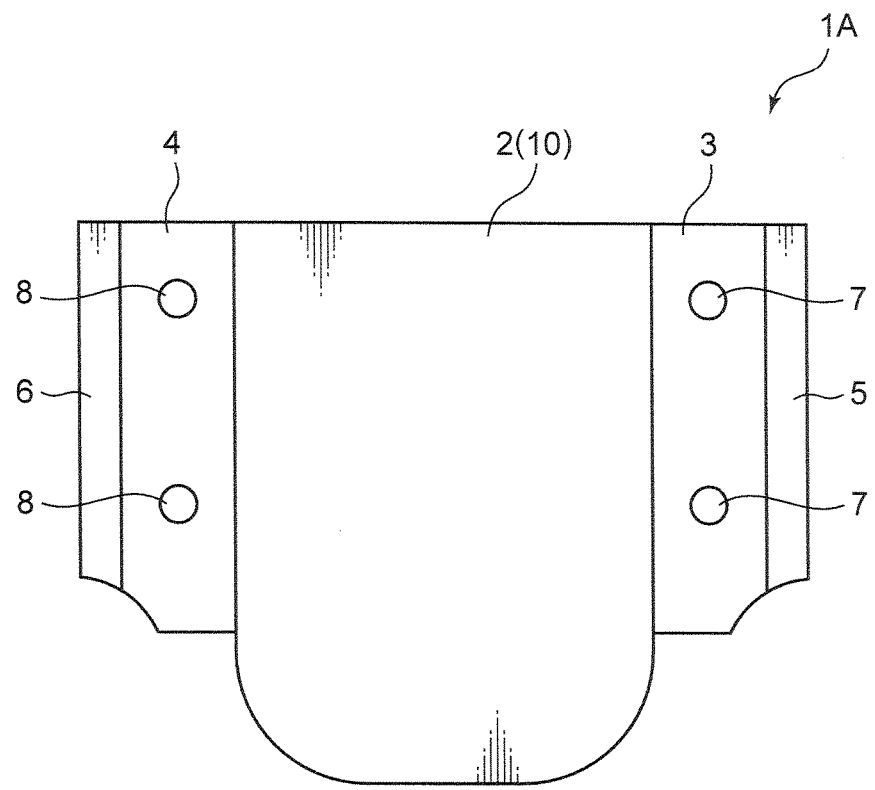
FIG. 1 is a front view illustrating a disposable diaper according to a first embodiment of the present invention.

FIG. 1 is a front view illustrating a disposable diaper according to a first embodiment of the present invention.

Figure 2:
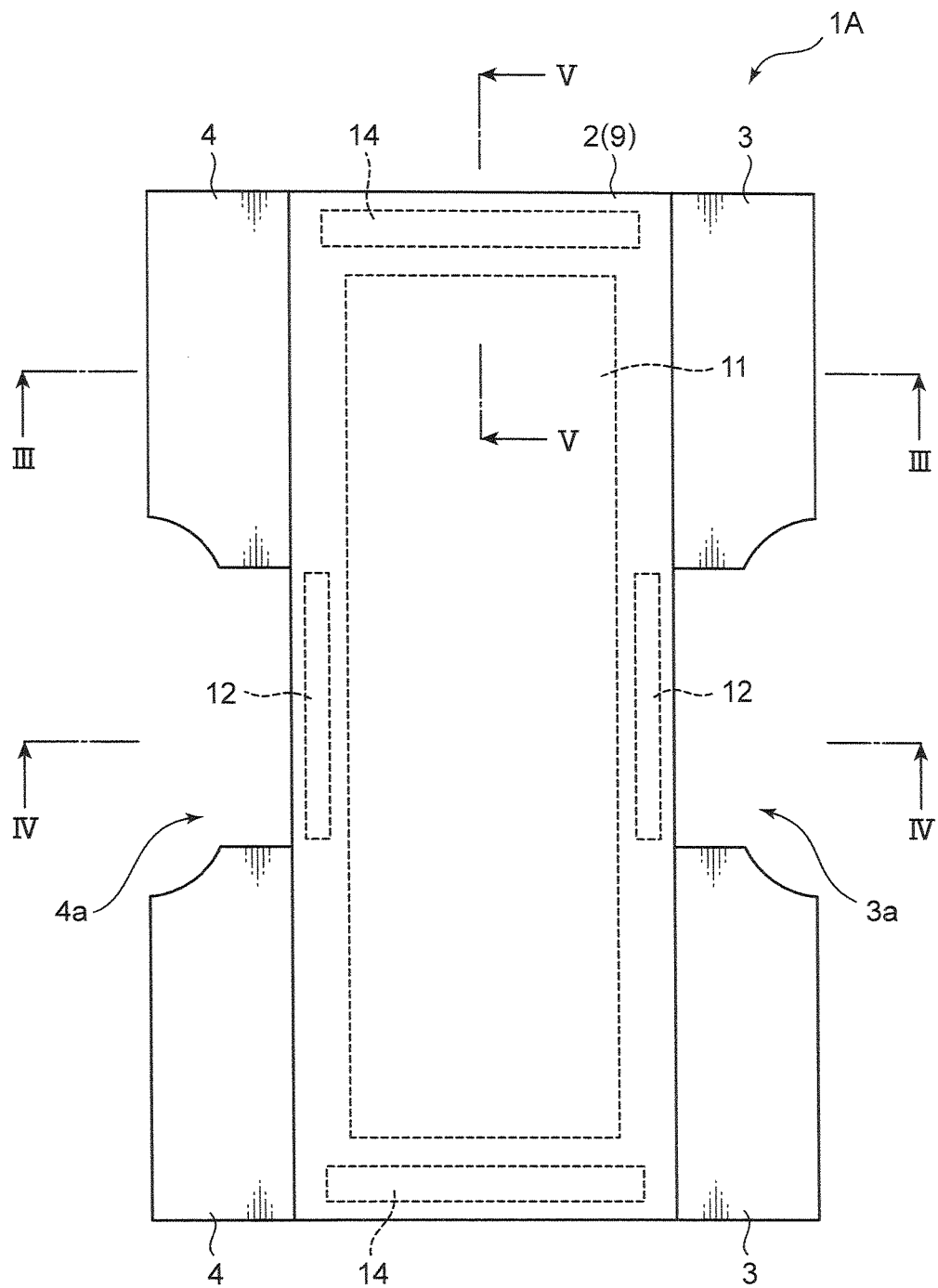
FIG. 2 is a plan view illustrating the disposable diaper in FIG. 1 in a state in which side sealed areas thereof are developed.

FIG. 2 is a plan view illustrating the disposable diaper in FIG. 1 in a state in which side sealed areas thereof are developed.

Referring to FIGS. 1 and 2, the disposable diaper 1A according to this embodiment, as one example of a wearing article, is a so-called pant-type diaper. More specifically, the disposable diaper 1A comprises a main body 2 adapted to extend from a front abdominal region to a rear dorsal region via a crotch region of a wearer, and four side panel segments 3, 3, 4, 4 for covering a lateral surface of a waist region of the wearer. The disposable diaper 1A is formed as a pant-type by, after folding the main body 2 in half, joining the pair of side panel segments 3, 3 together through a side sealed area 5, and joining the pair of side panel segments 4, 4 together through a side sealed area 6.

The disposable diaper 1A according to this embodiment further comprises a pair of temporarily joined areas 7, 7 each releasably joining the side panel segments 3, 3 together, and a pair of temporarily joined areas 8, 8 each releasably joining the side panel segments 4, 4 together. A positional relationship between the side panel segments 3, 3 and a positional relationship between the side panel segments 4, 4 are maintained by the temporarily joined areas 7, 8. This makes it possible to keep a half-folded state of the main body 2. Further, each of the temporarily joined areas 7, 8 releasably joins a respective pair of the side panel segments 3, 3 and the side panel segments 4, 4. Thus, a wearer can wear the disposable diaper 1A by releasing the joined state of the temporarily joined areas 7, 8.

With reference to FIGS. 1 to 5, a specific configuration of the disposable diaper 1A will be described below.

Figure 3:
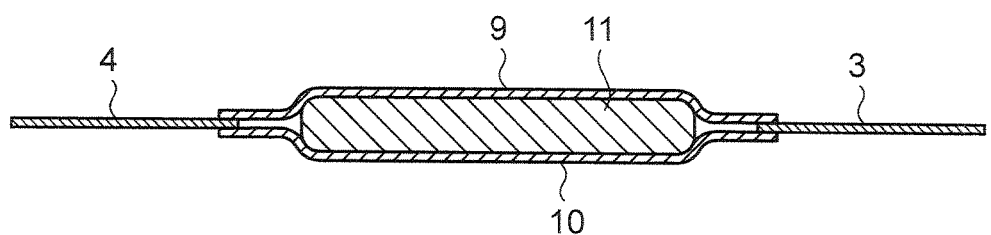
FIG. 3 is a sectional view taken along the line III-III in FIG. 2.
Figure 4:
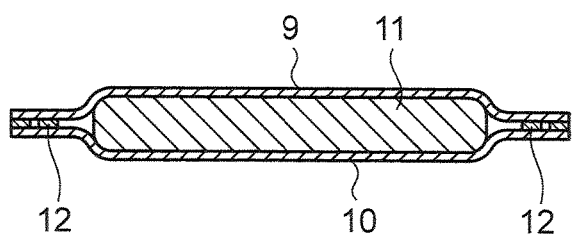
FIG. 4 is a sectional view taken along the line IV-IV in FIG. 2.
Figure 5:
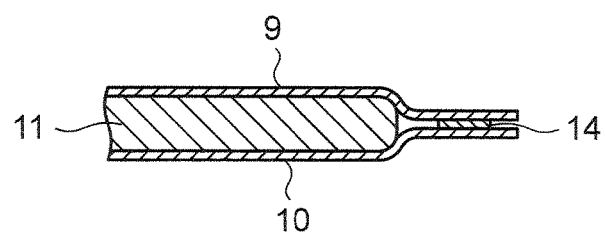
FIG. 5 is a sectional view taken along the line V-V in FIG. 2.

FIG. 3, FIG. 4 and FIG. 5 are, respectively, a sectional view taken along the line III-III in FIG. 2, a sectional view taken along the line IV-IV in FIG. 2, and a sectional view taken along the line V-V in FIG. 2.

The main body 2 is capable of absorbing bodily waste (e.g., urine) of a wearer, and has flexibility (stretchability and contractibility) in a desired position. More specifically, the main body 2 comprises: an absorbent body 11 capable of absorbing bodily waste of a wearer; a plurality of leg elastic members 12, 12 each provided at a position corresponding to a crotch region of the wearer; a pair of waist elastic members 14, 14 provided at respective positions corresponding to a front abdominal region and a rear dorsal region of the wearer; and an inner sheet 9 and an outer sheet 10 which sandwich therebetween the absorbent body 11, the leg elastic members 12, 12 and the waist elastic members 14, 14.

The inner sheet 9 is an approximately rectangular-shaped sheet which is disposed to face toward a body surface of the wearer during use or wearing of the disposable diaper, and has liquid-permeability. More specifically, as the inner sheet 9, it is possible to employ a nonwoven sheet or mesh sheet having liquid-permeability.

The outer sheet 10 is a sheet which is disposed to face outwardly with respect to the wearer during use or wearing of the disposable diaper, and has liquid-impermeability. More specifically, as the outer sheet 10, it is possible to employ a polyethylene film, or a nonwoven fabric having water repellency and breathability. Further, the outer sheet 10 is an approximately rectangular-shaped sheet formed in a size substantially equal to that of the inner sheet 9.

The absorbent body 11 is adapted to absorb liquid passing through the inner sheet 9. More specifically, the absorbent body 11 is formed by laminating and molding pulverized pulp or a mixture of pulverized pulp and highly-absorbent polymer. The absorbent body 11 is formed in an approximately rectangular or hourglass shape having a longitudinal dimension less than that of each of the sheets 9, 10 and a width dimension less than that of each of the sheets 9, 10. The absorbent body 11 is disposed between the two sheets 9, 10 to leave a non-installation zone along longitudinally opposite edge regions of each of the sheets 9, 10 and width-directionally (laterally) opposite edge regions of each of the sheets 9, 10. Then, as illustrated in FIG. 3, the absorbent body 11 is joined to the inner sheet 9 and the outer sheet 10 while being sandwiched between the two sheets 9, 10.

The leg elastic members 12, 12 are adapted to pull the main body 2 upwardly toward the crotch region of the wearer during the wearing to allow the main body 2 to be brought into close contact with the crotch region so as to suppress leakage of bodily waste from a gap between the main body 2 and the body surface of the wearer. More specifically, at least a portion of each of the leg elastic members 12, 12 is provided at a respective one of laterally opposite positions outside of the absorbent body 11 and between the side panel segments 3, 3 or between the side panel segments 4, 4. Each of the leg elastic members 12, 12 is attached to the main body 2 in a stretched state in a longitudinal direction of the main body 2. In this embodiment, as illustrated in FIG. 4, each of the leg elastic members 12, 12 is joined to the inner sheet 9 and the outer sheet 10 while being sandwiched between the two sheets 9, 10. As the leg elastic members 12, 12, it is possible to employ a sheet or thread made of polyurethane, natural rubber or thermoplastic resin.

Each of the waist elastic members 14, 14 is adapted to cause the main body 2 to be tightened against the front abdominal region or the rear dorsal region of the wearer, during the wearing so as to suppress slip-down of the disposable diaper 1A. More specifically, each of the waist elastic members 14, 14 is provided at a respective one of opposite positions longitudinally outward of the absorbent body 11, and attached to the main body 2 in a stretched state in a width or lateral direction of the main body 2. In this embodiment, as illustrated in FIG. 5, each of the waist elastic members 14, 14 is joined to the inner sheet 9 and the outer sheet 10 while being sandwiched between the two sheets 9, 10. As the waist elastic members 14, 14, it is possible to employ a sheet or thread made of polyurethane, natural rubber or thermoplastic resin.

Each of the side panel segments 3, 3 extends from a respective one of longitudinally (front-rear directionally) opposite end portions of the main body 2, laterally in one direction (rightwardly in FIGS. 1 and 2), and has flexibility in the lateral direction. The side panel segments 3, 3 are disposed to define a leg-hole space 3a therebetween. The leg-hole space 3a is used as a lag hole by joining together right edge portions of the side panel segments 3, 3 by the side sealed area 5. The side panel segments 3, 3 are formed with a pair of temporarily joined areas 7, 7 each releasably joining the side panel segments 3, 3 together. Each of the temporarily joined areas 7, 7 is formed by externally heating and/or pressing superimposed portions of the side panel segments 3, 3, as described in detailed later. In this embodiment, as illustrated in FIG. 3, each of the side panel segments 3, 3 is joined to the inner sheet 9 and the outer sheet 10 while being sandwiched between the two sheets 9, 10 at a position rightward of the absorbent body 11. As the side panel segments 3, 3, it is possible to employ: a stretchable film made of one or a mixture of at least two selected from the group consisting of polystyrene based block copolymer, polyisoprene based block copolymer, polybutadiene based block copolymer, ethylene based copolymer, natural rubber and urethane; a stretchable nonwoven fabric; a laminate of the stretchable film and the stretchable nonwoven fabric; or a laminate of rubber thread and the stretchable nonwoven fabric.

Each of the side panel segments 4, 4 extends from a respective one of longitudinally (front-rear directionally) opposite end portions of the main body 2, laterally in one direction (leftwardly in FIGS. 1 and 2), has flexibility in the lateral direction. The side panel segments 4, 4 are disposed to define a leg-hole space 4a therebetween. The leg-hole space 4a is used as a lag hole by joining together left edge portions of the side panel segments 4, 4 by the side sealed area 6. The side panel segments 4, 4 are formed with a pair of temporarily joined areas 8, 8 each releasably joining the side panel segments 4, 4 together. Each of the temporarily joined areas 8, 8 is formed by externally heating and/or pressing superimposed portions of the side panel segments 4, 4, as described in detailed later. In this embodiment, as illustrated in FIG. 3, each of the side panel segments 4, 4 is joined to the inner sheet 9 and the outer sheet 10 while being sandwiched between the two sheets 9, 10 at a position leftward of the absorbent body 11. As the side panel segments 4, 4, it is possible to employ: a stretchable film made of one or a mixture of at least two selected from the group consisting of polystyrene based block copolymer, polyisoprene based block copolymer, polybutadiene based block copolymer, ethylene based copolymer, natural rubber and urethane; a stretchable nonwoven fabric; a laminate of the stretchable film and the stretchable nonwoven fabric; or a laminate of rubber thread and the stretchable nonwoven fabric.

Figure 6:
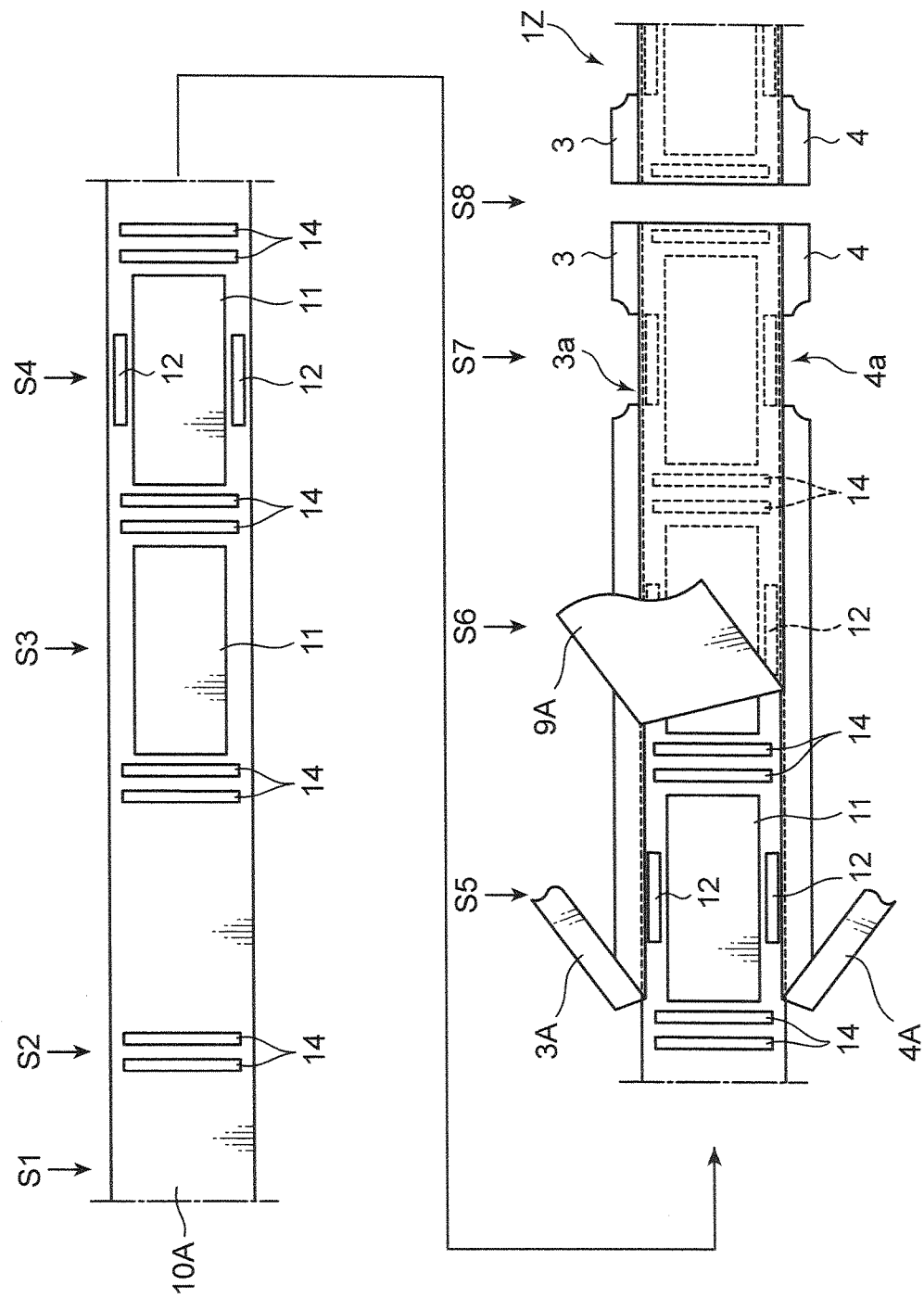
FIG. 6 is a process chart of a production method for the disposable diaper in FIG. 1.
Figure 7:
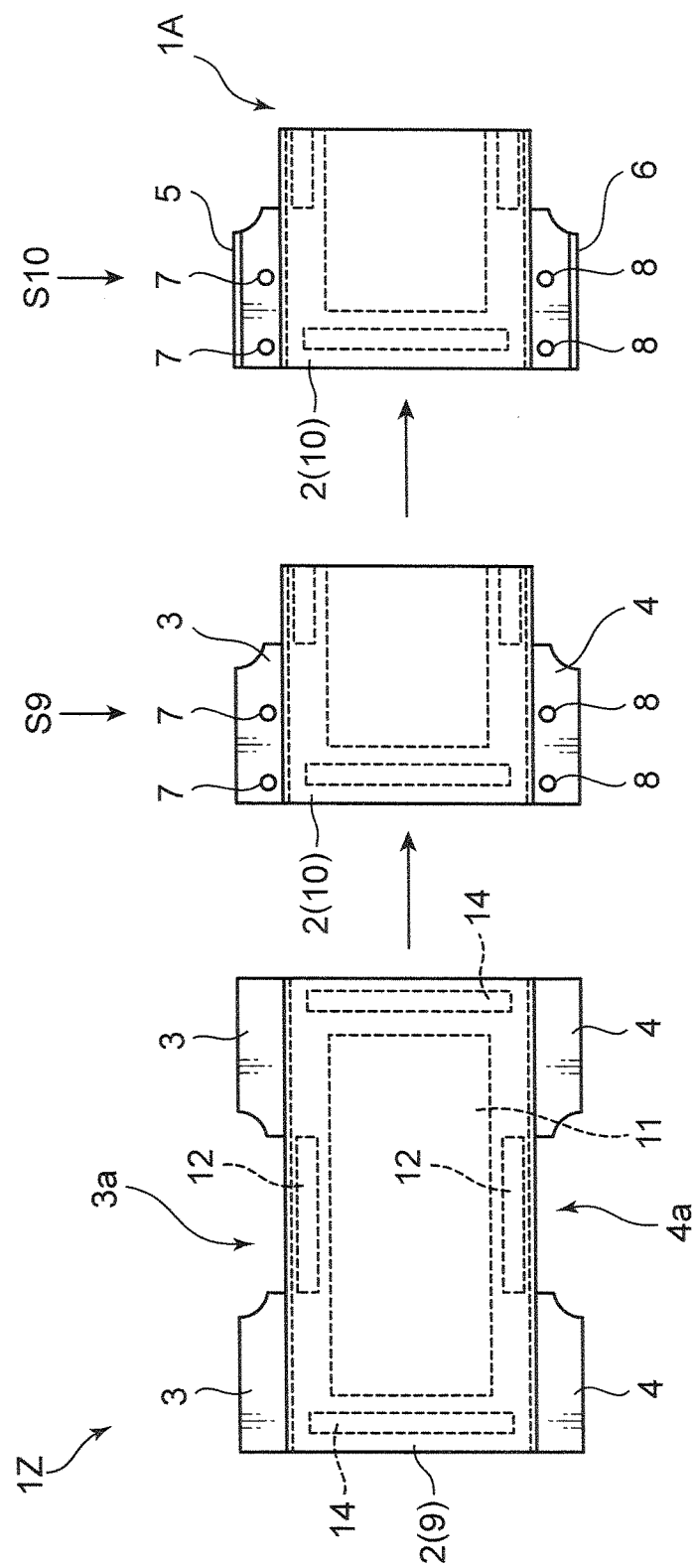
FIG. 7 is a process chart of the production method for the disposable diaper in FIG. 1, which illustrates a process following the process in FIG. 6.

With reference to FIGS. 6 and 7, a production method for the above disposable diaper 1A will be described below.

FIG. 6 is a process chart of a production method for the disposable diaper in FIG. 1. FIG. 7 is a process chart of the production method for the disposable diaper in FIG. 1, which illustrates a process following the process in FIG. 6.

The production method for the disposable diaper 1A primarily comprises the following steps S1 to S10.

<Step S1>

In Step S1, an outer sheet strip 10A for forming the outer sheet 10 is continuously conveyed in a longitudinal direction of the outer sheet strip 10A.

<Step S2>

In Step S2, the waist elastic members 14 is joined onto the outer sheet strip 10A which is continuously being conveyed. More specifically, in the Step S2, a plurality of pairs of the waist elastic members 14 are disposed on the outer sheet strip 10A at intervals of a distance corresponding to a longitudinal dimension of the absorbent body 11, on a pair-by-pair basis. In this process, each of the waist elastic members 14 is attached onto the outer sheet strip 10A in a state in which it is stretched in a width direction of the outer sheet strip 10A. Further, the waist elastic members 14 in a pair to be attached in the Step S2 are disposed in spaced-apart relation to each other in the longitudinal direction of the outer sheet strip 10A.

<Step S3>

In Step S3, the absorbent body 11 is joined onto the outer sheet strip 10A which is continuously being conveyed. More specifically, the absorbent body 11 is disposed between adjacent two of the pairs of waist elastic members 14 in a posture where the longitudinal direction thereof is oriented along the longitudinal direction of the outer sheet strip 10A.

<Step S4>

In Step S4, a pair of the leg elastic members 12 is joined onto the outer sheet strip 10A which is continuously being conveyed. More specifically, in the Step S4, the leg elastic members 12 in the pair are disposed at a longitudinally central position of the absorbent body 11 on the outer sheet strip 10A and are one-by-one disposed at respective laterally opposite positions outside of the absorbent body 11. Each of the leg elastic members 12 is attached onto the outer sheet strip 10A in a state in which it is stretched in the longitudinal direction of the outer sheet strip 10A.

<Step S5>

In Step S5, a side panel strip 3A for forming the side panel segment 3, and a side panel strip 4A for forming the side panel segment 4, are joined onto the outer sheet strip 10A which is continuously being conveyed. More specifically, each of the side panel strips 3A, 4A is continuously fed in a posture where a longitudinal direction thereof is oriented along the longitudinal direction of the outer sheet strip 10A, and joined onto a respective one of opposite edge portions of the outer sheet strip 10A outside of the leg elastic members 12. That is, each of the side panel strips 3A, 4A is joined to the outer sheet strip 10A while protruding from the outer sheet strip 10A.

<Step S6>

In Step S6, an inner sheet strip 9A for forming the inner sheet 9 is joined onto the outer sheet strip 10A which is continuously being conveyed. More specifically, the inner sheet strip 9A is continuously fed in a posture where a longitudinal direction thereof is oriented along the longitudinal direction of the outer sheet strip 10A, and joined to the outer sheet strip 10A in a state in which a position of the inner sheet strip 9A in the width direction is adjusted to a position of the outer sheet strip 10A in the width direction. By the Step S6, the elastic members 12, 14 and the absorbent body 11 are entirely sandwiched between the sheet strips 9A, 10A, and an edge portion of each of the side panel strips 3A, 4A is sandwiched between the sheet strips 9A, 10A.

<Step S7>

In Step S7, each of the side panel strips 3A, 4A is partially cut away to form a respective one of the spaces 3a, 4a. More specifically, each of the side panel strips 3A, 4A is cut away over a predetermined range in the longitudinal direction of the side panel strips 3A, 4A, including the longitudinally central position of the absorbent body 11.

<Step S8>

In Step S8, the sheet strips 9A, 10A and the side panel strips 3A, 4A are cut off to form an developed module 1Z of a disposable diaper. Specifically, the sheet strips 9A, 10A and the side panel strips 3A, 4A are cut at a position between the pair of adjacent waist elastic members 14. By the Step S8, the developed module 1Z is formed in which the side panel strips 3A, 4A are segmentalized into the four side panel segments 3, 3, 4, 4.

<Step S9>

Referring to FIG. 7, in Step S9, the main body 2 of the developed module 1Z is folded in half along a longitudinally central position thereof, and kept in a half-folded state. More specifically, by use of an after-mentioned production apparatus, the main body 2 is folded in half, and temporarily joined areas 7, 8 are formed in respective ones of the pairs of side panel segments 3, 3 and side panel segments 4, 4 superimposed by the half-folding.

<Step S10>

In Step S10, a side sealed area 5 is formed along edge portions of the side panel segments 3, 3, and a side sealed area 6 is formed along edge portions of the side panel segments 4, 4, thereby completing the disposable diaper 1A.

As described above, in the production apparatus according to this embodiment, the developed module 1Z can be produced by the Steps S1 to S8 (developed module preparing step), and the disposable diaper 1A can be produced by subjecting the developed module 1Z to the Steps S9 and S10. In the production method according to this embodiment, the following production apparatus 20 (particularly, aftermentioned folding unit 22 and conveying and sealing unit 23) are prepared (suction-holding section preparing step) so as to perform the Steps S9 and S10.

A production apparatus for performing the Steps S8 to S10 will be described below.

Figure 8:
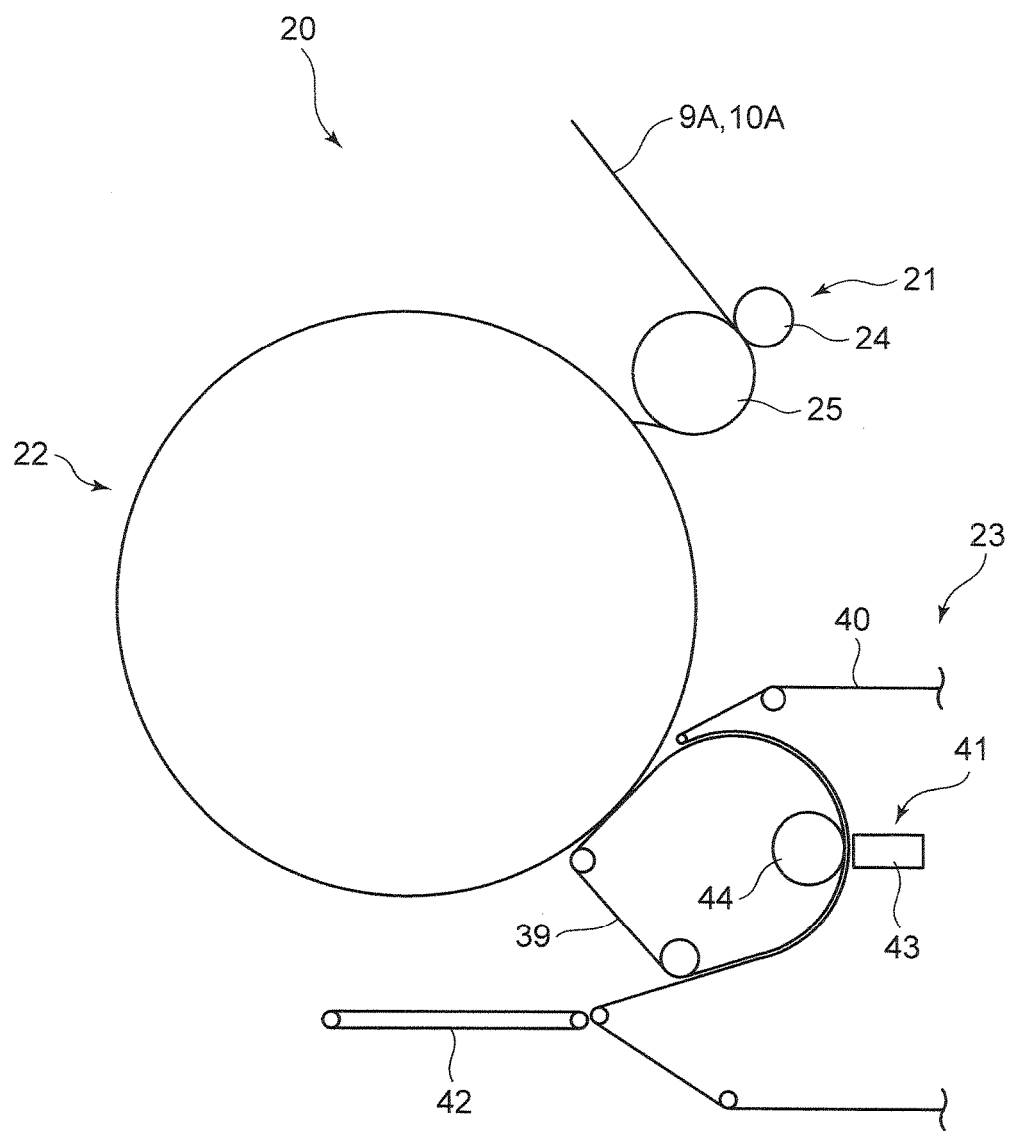
FIG. 8 is a schematic diagram illustrating a general configuration of a production apparatus for performing Steps S8 to S10 in FIGS. 6 and 7.

FIG. 8 is a schematic diagram illustrating a general configuration of the production apparatus for performing the Steps S8 to S10 in FIGS. 6 and 7.

Referring to FIG. 8, the production apparatus 20 comprises a cutting unit 21 for performing the Step S8, a folding unit 22 for performing the Step S9, and a conveying and sealing unit 23 for performing the Step S10.

The cutting unit 21 is adapted to cut the inner sheet strip 9A, the outer sheet strip 10A and the side panel strips 3A, 4A to form the developed module 1Z. More specifically, the cutting unit 21 comprises a rotary cutter 24, and a vacuum roll 25 disposed in opposed relation to the rotary cutter 24. The rotary cutter 24 has a cutting blade capable of cutting the side panel strips 3A, 4A by nipping the side panel strips 3A, 4A and the sheet strips 9A, 10A between the vacuum roll 25 and the rotary cutter 24. The vacuum roll 25 has a body wall capable of suction-holding the side panel strips 3A, 4A and the sheet strips 9A, 10A. The developed module 1Z after the cutting by the rotary cutter 24 is transferred to the folding unit 22 by rotating the vacuum roll 25 while suction-holding the developed module 1Z by the body wall of the vacuum roll 25.

Figure 9:
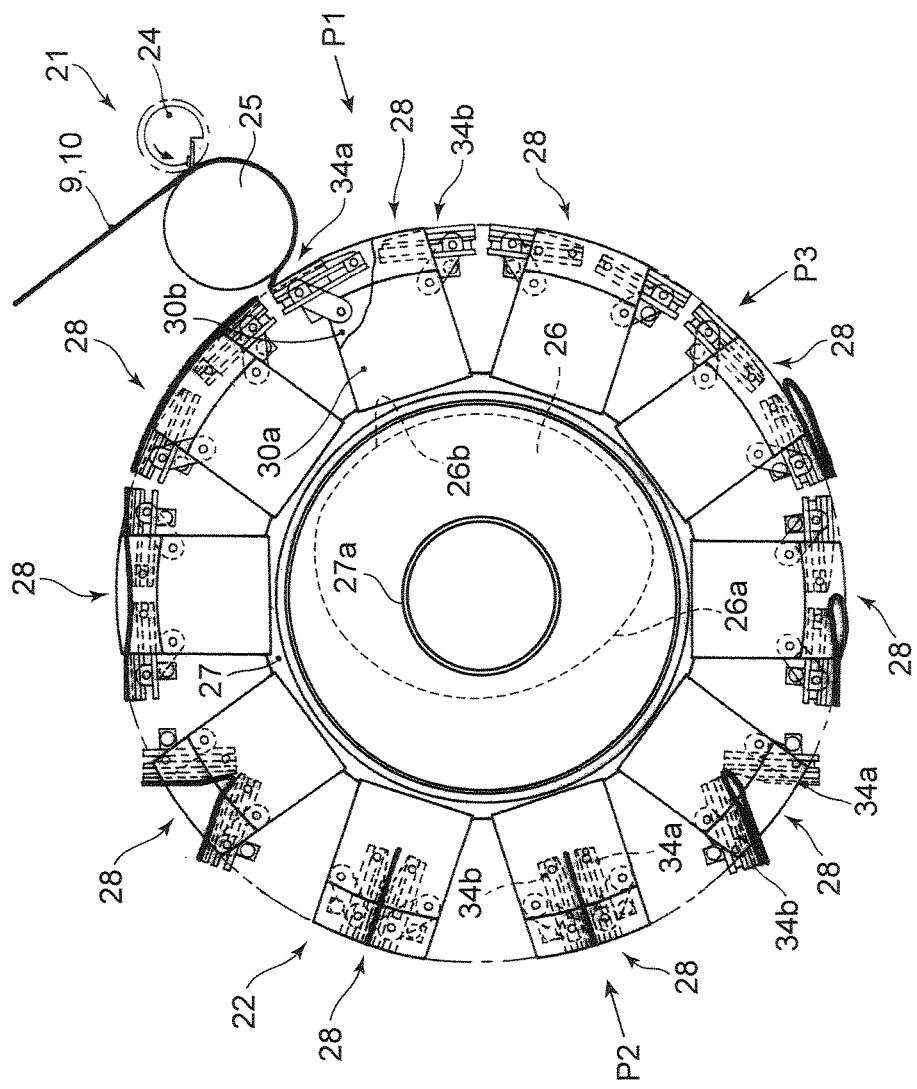
FIG. 9 enlargedly illustrates a folding unit in FIG. 8.

FIG. 9 enlargedly illustrates the folding unit in FIG. 8.

The folding unit 22 comprises a camshaft 26, a drum (support member) 27 disposed around the camshaft 26 to rotationally drive about a rotary shaft 27a, and ten folding sub-units 28 supported around the drum. The camshaft 26 has an outer surface in which a circular cylindrical surface 26b concentric with the rotary shaft 27a of the drum 27, and a cam surface 26a more inclined toward the rotary shaft 27a than the circular cylindrical surface 26b are continuously formed. The drum 27 covers over the entire outer periphery of the camshaft 26 from the outside of the camshaft 26, and supports each of the folding sub-units 28 in such a manner that each of the folding sub-units 28 protrudes outwardly. Each of the folding sub-units 28 is adapted, with respect to the developed module 1Z transferred from the cutting unit 21, to fold the main body 2 in half, and form the temporarily joined areas 7, 8 (see FIG. 1) in the side panel segments 3, 3, 4, 4. More specifically, the folding sub-unit 28 is adapted, after receiving the developed module 1Z from the cutting unit 21 at a rotational position P1 around the rotary shaft 27a, to gradually fold the main body 2 of the developed module 1Z along with a counterclockwise (in FIG. 9) rotation of the drum 27 from the rotational position P1, and finally fold the main body 2 in half at a rotational position P2. Further, the folding sub-unit 28 is adapted to transfer the half-folded developed module 1Z to the conveying and sealing unit 23 at a rotational position P3 where the drum 27 is further rotated from the rotational position P2 in the counterclockwise (in FIG. 9) direction.

Figure 10:
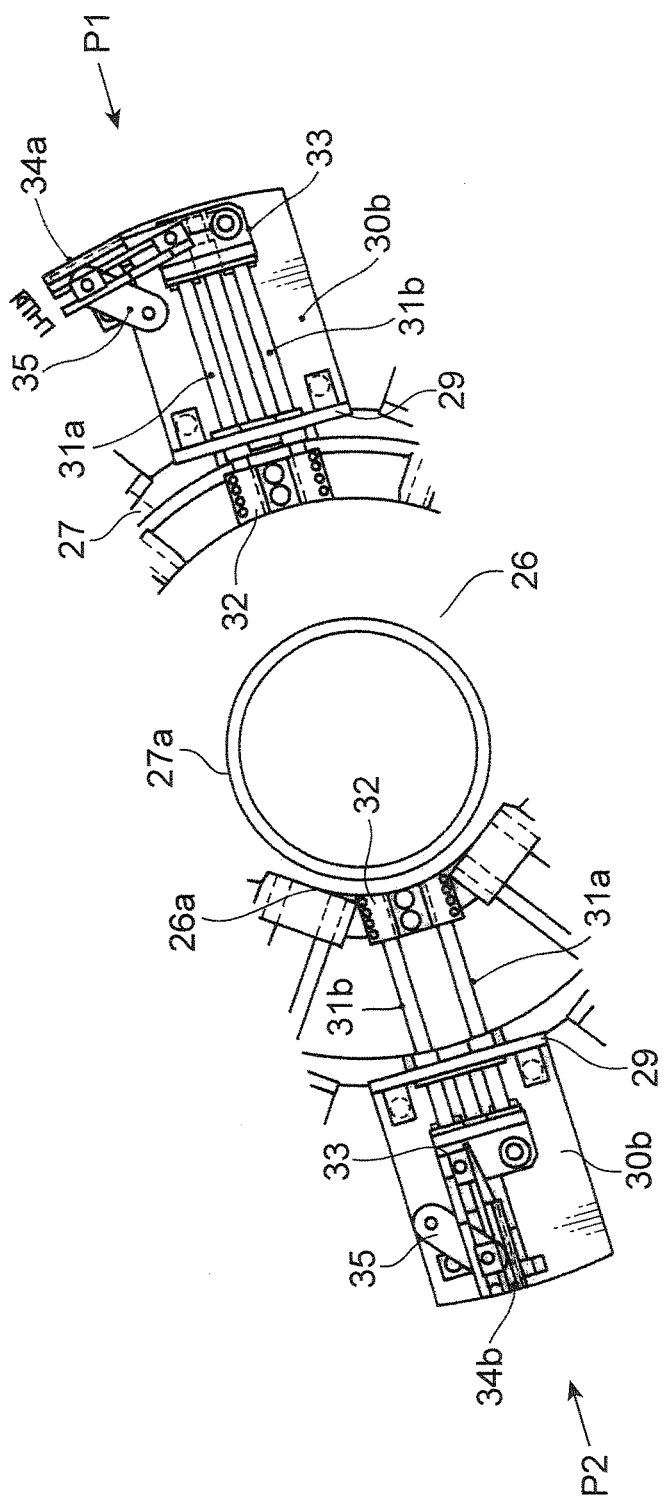
FIG. 10 is a schematic diagram enlargedly illustrating two folding sub-units which are, respectively, at rotational positions P1, P2 in FIG. 9.

With reference to FIGS. 9 and 10, a specific configuration of the folding sub-unit 28 will be described below. FIG. 10 is a schematic diagram enlargedly illustrating the folding sub-units 28, which are, respectively, at the rotational positions P1, P2 in FIG. 9.

The folding sub-unit 28 comprises: a base 29 fixed to an outer surface of the drum 27; a pair of support plates 30a, 30b each standingly provided on the base 29; a pair of sliding shafts 31a, 31b each provided to penetrate through the base 29 and the drum 27; a slider 32 fixed to an inner end of each of the sliding shafts 31a, 31b located inside the drum 27; a mounting member 33 fixed to an outer end of each of the sliding shafts 31a, 31b located outside the drum 27; a first suction-holding section 34a and a second suction-holding section 34b each attached to the mounting member 33 swingably about an axis parallel to the rotary shaft 27a; and a pair of links 35 each coupling one of the suction-holding sections 34a, 34b and a corresponding one of the support plates 30a, 30b together. In FIG. 10, the suction-holding sections 34b at the rotational position P1, and the suction-holding sections 34a at the rotational position P2 are omitted.

Each of the sliding shafts 31a, 31b is biased toward the rotary shaft 27a by a non-illustrated biasing member. Thus, the slider 32 fixed to the inner end of each of the sliding shafts 31a, 31b is continually pressed against the outer surface of the camshaft 26. Therefore, when the slider 32 is slidingly moved along the outer surface of the camshaft 26 along with rotation of the drum 27, each of the sliding shafts 31a, 31b is displaced in a radial direction of the drum 27. Each of the links 35 has a first end attached to a respective one of the suction-holding sections 34a, 34b rotatably about an axis parallel to the rotary shaft 27a, and a second end attached to a respective one of the support plates 30a, 30b rotatably about an axis parallel to the rotary shaft 27a. Thus, when the sliding shafts 31a, 31b are displaced radially in a direction away from a center of the drum 27, the suction-holding sections 34a, 34b are swingingly moved with respect to the mounting member 33 and the support plates 30a, 30b via the links 35. This allows the suction-holding sections 34a, 34b to be opened in such a manner that respective surfaces of the suction-holding sections 34a, 34b are aligned side-by-side while facing the same side (the suction-holding section positioning step). On the other hand, when the sliding shafts 31a, 31b are displaced radially in a direction approaching the center of the drum 27, the suction-holding sections 34a, 34b are swingingly moved with respect to the mounting member 33 and the support plates 30a, 30b via the links 35. This allows the suction-holding sections 34a, 34b to be closed in such a manner that the respective surfaces of the suction-holding sections 34a, 34b face each other (the half-folding step).

Figure 11:
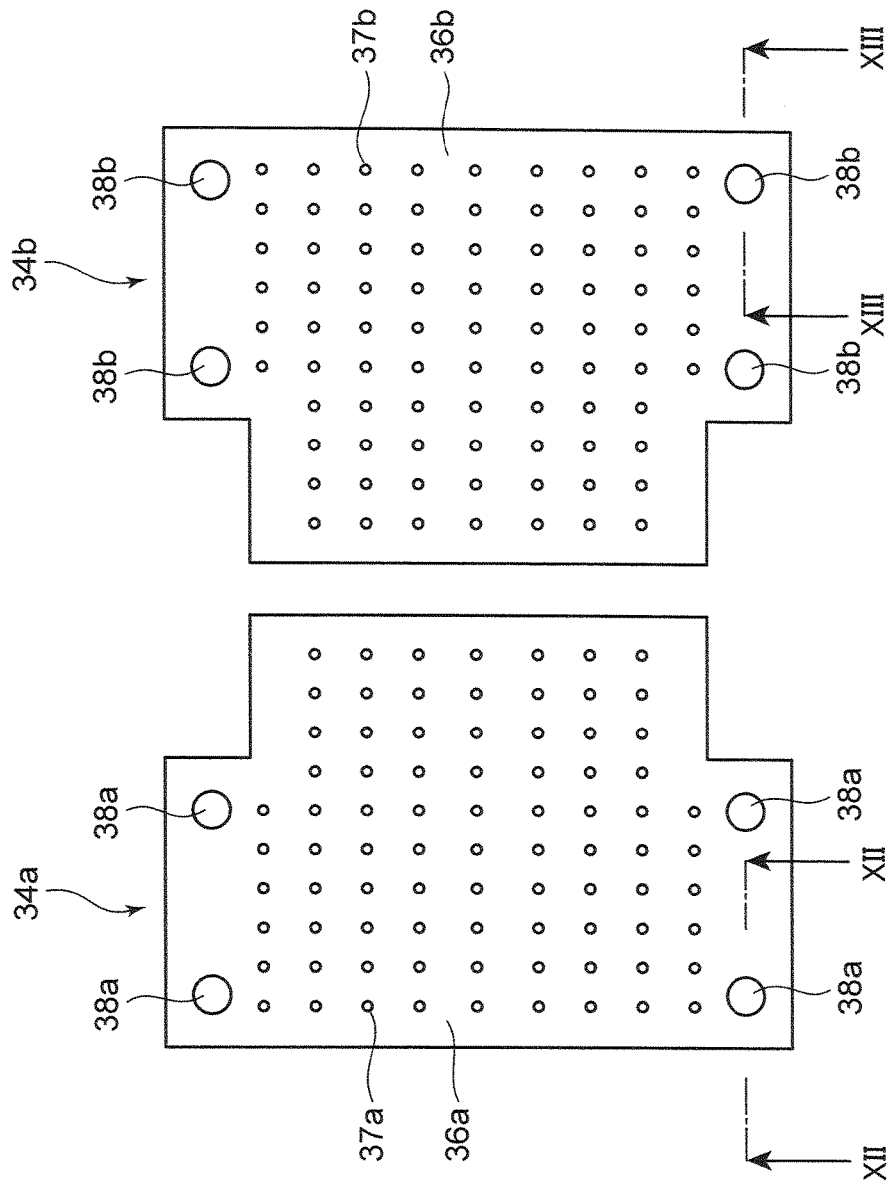
FIG. 11 is a plan view enlargedly illustrating suction-holding sections in FIGS. 9 and 10.

FIG. 11 is a plan view enlargedly illustrating the suction-holding sections in FIGS. 9 and 10.

Referring to FIG. 11, the first suction-holding section 34a is adapted to suction-hold a forward surface of the developed module 1Z (a region of a surface of the developed module 1Z forward of a folding line). More specifically, the first suction-holding section 34a comprises a section body 36a having a planar T shape corresponding a shape of a combination of the front end portion of the main body 2 and the two side panel segments 3, 4 in the developed module 1Z, and a plurality of suction holes 37a formed in a surface (first suction-holding surface) of the section body 36a. The first suction-holding section 34a is adapted to suck air from the suction holes 37a according to a non-illustrated suction source, thereby suction-holding a forward portion of the developed module 1Z by the surface of the section body 36a.

Similarly, the second suction-holding section 34b is adapted to suction-hold a rearward surface of the developed module 1Z (a region of a surface of the developed module 1Z rearward of the folding line). More specifically, the suction-holding section 34b comprises a section body 36b having a planar T shape corresponding a shape of a combination of the rear end portion of the main body 2 and the two side panel segments 3, 4 in the developed module 1Z, and a plurality of suction holes 37b formed in a surface (second suction-holding surface) of the section body 36b. The second suction-holding section 34b is adapted to suck air from the suction holes 37b according to a non-illustrated suction source, thereby suction-holding the rearward surface of the developed module 1Z by the surface of the section body 36b.

Figure 12:
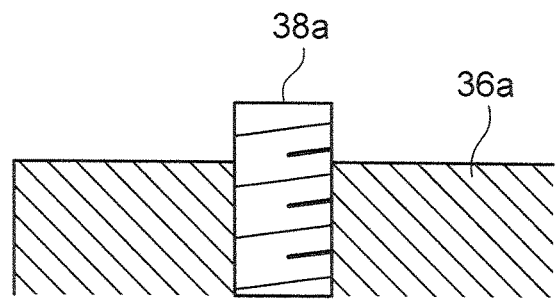
FIG. 12 is a sectional view taken along the line XII-XII in FIG. 11.

The suction-holding section 34a in this embodiment further comprises a protruding element 38a which protrudes from the surface (first suction-holding surface) of the section body 36a and is capable of compressing superimposed portions of the developed module 1Z in cooperation with the second suction-holding section 34b. FIG. 12 is a sectional view taken along the line XII-XII in FIG. 11.

Referring to FIG. 12, the protruding element 38a is composed of a columnar screw member having an external thread formed in an outer peripheral surface thereof. This protruding element 38a is screwed with a screw hole formed in the section body 36a. Thus, a level of screw-in of the protruding element 38a with respect to the section body 36a can be changed so as to adjust an amount of protrusion of the protruding element 38a from the section body 36a.

Figure 13:
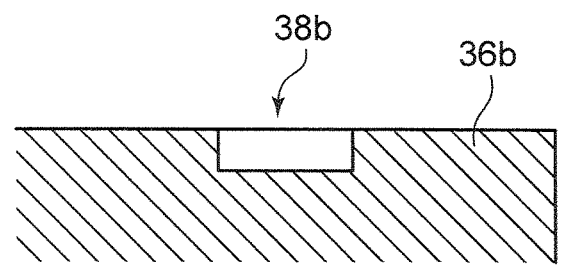
FIG. 13 is a sectional view taken along the line XIII-XIII in FIG. 11.
Figure 14:
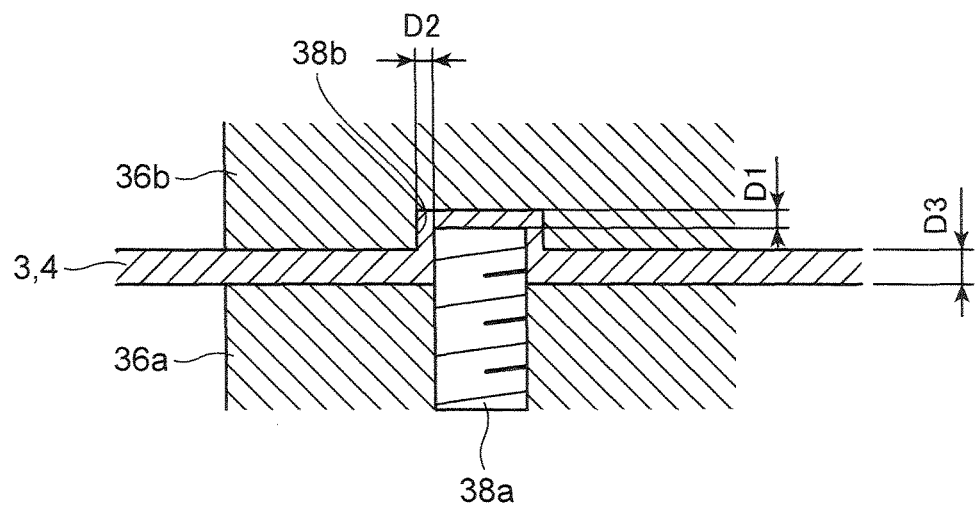
FIG. 14 is a sectional view illustrating a state in which a developed module is compressed between the suction-holding sections.

On the other hand, the suction-holding section 34b in this embodiment further comprises a recess 38b which is concaved from the surface of the section body 36b and capable of allowing the protruding element 38a to be engaged thereinto while interposing the superimposed portions of the developed module 1Z therebetween. FIG. 13 is a sectional view taken along the line XIII-XIII in FIG. 11. FIG. 14 is a sectional view illustrating a state in which the developed module IZ is compressed between the suction-holding sections 34a, 34b.

With reference to FIGS. 13 and 14, the recess 38b is formed in a size which allows a predetermined gap to be defined with respect to the protruding element 38a when the protruding element 38a is inserted thereinto. More specifically, each of a distance D1 between a distal edge face of the protruding element 38a and a bottom surface of the recess 38b, and a distance D2 between the outer peripheral surface of the protruding element 38a and an inner peripheral surface of the recess 38b, in the closed state of the suction-holding sections 34a, 34b, is set to be less than a thickness dimension of the superimposed portions of the developed module 1Z.

Thus, the superimposed portions (side panel segment pairs 3, 4) of the developed module 1Z are compressed between an outer surface of the protruding element 38a and an inner surface of the recess 38b, and releasably joined together (the temporarily joined areas 7, 8 are formed, respectively, in the side panel segment pairs 3, 4: the temporarily joining step). A distance D3 between the surface of the first suction-holding section 34a and the surface of the second suction-holding section 34b in the closed state of the suction-holding sections 34a, 34b is set to be greater than each of the distances D1, D2, more specifically, equal to or slightly greater than the thickness dimension of the superimposed portions of the developed module 1Z.

In this embodiment, the first suction-holding section 34a is provided with the protruding element 38a, and the second suction-holding section 34b is provided with the recess 38b. Alternatively, the first suction-holding section 34a is provided with the recess 38b, and the second suction-holding section 34b is provided with the protruding element 38a. Further, each of the first suction-holding section 34a and the second suction-holding section 34b may be provided with the protruding element 38a and the recess 38b in such a manner that each of the protruding elements 38a can be engaged into a counterpart one of the recesses 38b.

Figure 15:
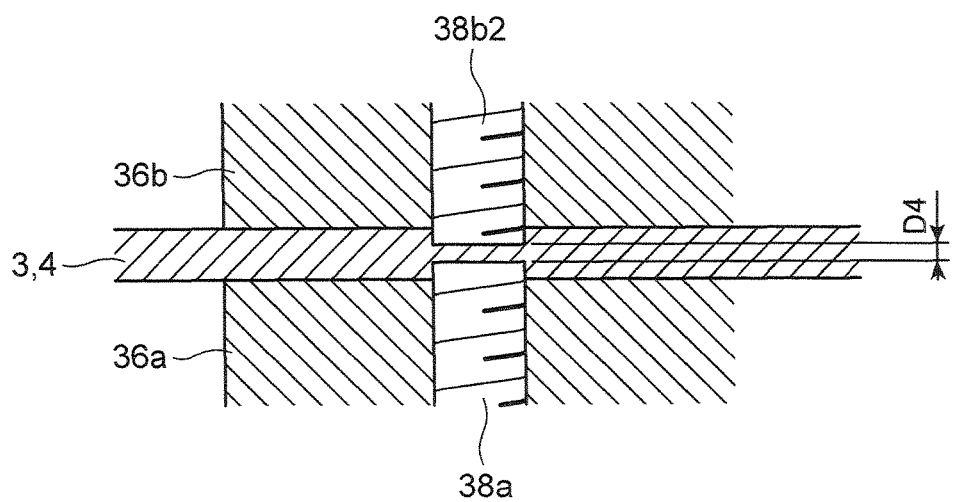
FIG. 15 is a sectional view illustrating an example of modification of the suction-holding sections in FIG. 11.

In this embodiment, each of the temporarily joined areas 7, 8 is formed in the superimposed portions of the developed module 1Z by allowing the protruding element 38a to be engaged into the recess 38b. In the present invention, a mechanism for forming each of the temporarily joined areas 7, 8 is not limited to the combination of the protruding element 38a and the recess 38b. FIG. 15 is a sectional view illustrating an example of modification of the suction-holding sections in FIG. 11. In the modification illustrated in FIG. 15, not only the first suction-holding section 34a, but also the second suction-holding section 34b is provided with a protruding element 38b2. In this case, when the suction-holding sections 34a, 34b are closed, the distal edge face of the protruding element 38a and a distal edge face of the protruding element 38b2 are disposed in opposed, spaced-apart relation to each other by a distance D4. This distance D4 is set to be less than the thickness of the superimposed portions of the developed module 1Z. Thus, the superimposed portions of the developed module 1Z are compressed between the protruding element 38a and the protruding element 38b2, and releasably joined together. In the modification in FIG. 15, the developed module 1Z is compressed between the protruding elements 38a, 38b2. Alternatively, only one of the suction-holding sections 34a, 34b may be provided with a protruding element, while omitting a protruding element for the other suction-holding section, wherein the superimposed portions of the developed module 1Z are compressed between the protruding element and a surface of the other suction-holding section.

In this embodiment, each of the temporarily joined areas 7, 8 is formed by compressing the superimposed portions of the developed module 1Z. Alternatively or additionally, the temporarily joined areas 7, 8 may be formed by heating the superimposed portions of the developed module 1Z. More specifically, at least one of the suction-holding sections 34a, 34b may be provided with a heater for heating at least one of the inner surfaces of the protruding element 38a and the recess 38b.

Figure 16:
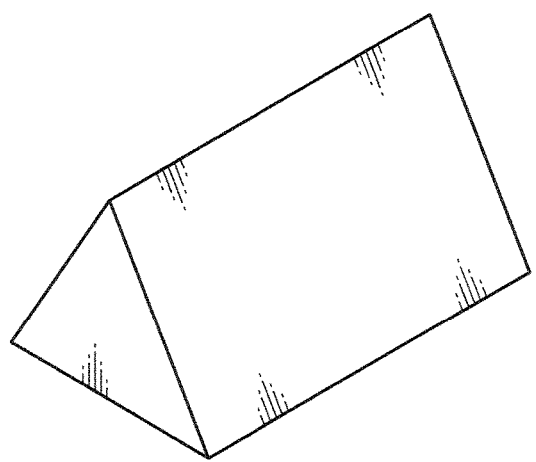
FIG. 16 is a sectional view illustrating an example of modification of a protruding element in FIG. 11.

In this embodiment, the protruding elements 38a, 38b2 each having a columnar shape are described as an example of the protruding element. Alternatively, a triangular prism-shaped protruding element as illustrated in FIG. 16 may be employed. The protruding element illustrated in FIG. 16 is disposed in one of the suction-holding sections 34a, 34b in a posture where a top ridge thereof is oriented toward the other suction-holding section in the closed state of the suction-holding sections 34a, 34b. When this protruding element is employed, a contact area with respect to the developed module 1Z can be reduced as compared to the case where the distal end face of the aforementioned columnar-shaped protruding element is pressed against the developed module 1Z. Thus, it becomes possible to more strongly compress the superimposed portions of the developed module 1Z.

As above, in the folding unit 22, the main body 2 of the developed module 1Z can be folded in half while forming the temporarily joined areas 7, 8 in the side panel segment 3, 4 of the half-folded developed module 1Z, by closing the suction-holding sections 34*a*, 34*b* as illustrated at the rotational position P2 in FIG. 9. Thus, even when the suction-holding sections 34*a*, 34*b* are opened between the rotational position P2 and the rotational position P3, the temporarily joined areas 7, 8 allows the half-folded state of the developed module 1Z to be maintained. Then, the half-folded developed module 1Z is transferred to the conveying and sealing unit 23 at the rotational position P3.

Referring to FIG. 8, the conveying and sealing unit 23 comprises: a first conveyer 39 for receiving the developed module 1Z from the folding unit 22; a second conveyer 40 disposed in opposed relation to a part of the first conveyer 39; a side sealing section 41 for forming the side sealed areas 5, 6 in the side panels 3, 4 of the developed module 1Z which is being conveyed by the conveyers 39, 40; and a third conveyer 42 for receiving a disposable diaper 1A from the second conveyer 40.

Figure 17:
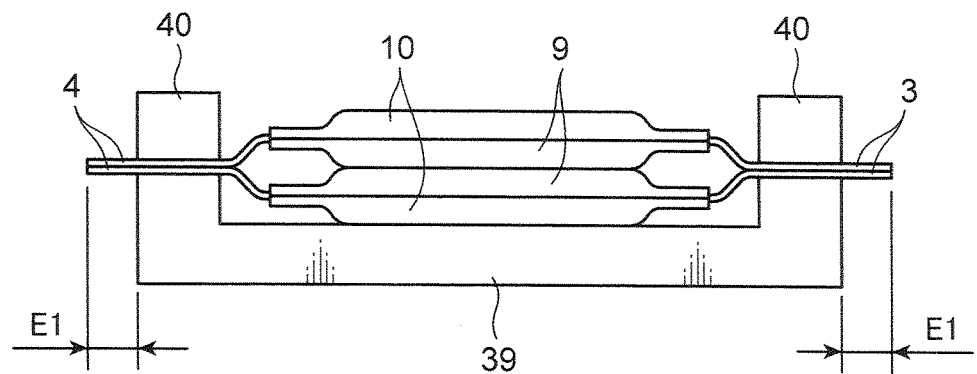
FIG. 17 is a schematic diagram illustrating a conveyance state of the developed module using a first conveyer and a second conveyer.

The first conveyer 39 is arranged in a loop shape having a portion extending in a tangential direction with respect to each of the folding sub-units 28 of the folding unit 22, and a portion making a U-turn from the tangential portion. The second conveyer 40 is disposed in opposed to the U-turn portion of the first conveyer 39. Thus, the developed module 1Z transferred to the first conveyer 39 is conveyed toward a downstream side while being clamped between the first conveyer 39 and the second conveyer 40. With reference to FIG. 17, specific configurations of the first conveyer 39 and the second conveyer 40 will be described below.

FIG. 17 is a schematic diagram illustrating a conveyance state of the developed module IZ using the first conveyer 39 and the second conveyer 40.

The first conveyer 39 has a portion for supporting the half-folded main body 2 from therebelow, and a portion for supporting superimposed portions of each of the side panel segment pairs 3, 4 from therebelow, and is adapted to be circulated along a predetermined pathway. The second conveyer 40 has a portion for pressing the side panel segment 3, 4 from thereabove, in such a manner as to clamp the side panel segment 3, 4 in cooperation with the first conveyer 39, and is adapted to be circulated along a predetermined pathway. The first conveyer 39 and the second conveyer 40 are arranged to vertically clamp the side panel segment 3, 4 in such a manner as to allow lateral edge portions of the side panel segment 3, 4 to be exposed as a side sealing region E1.

As above, the half-folded developed module 1Z is conveyed in a state in which superimposed portions of each of the side panel segment pairs 3, 4 are clamped by the conveyers 39, 40. Thus, the developed module 1Z is conveyed to the side sealing section 41 while being kept in the half-folded state.

Figure 18:
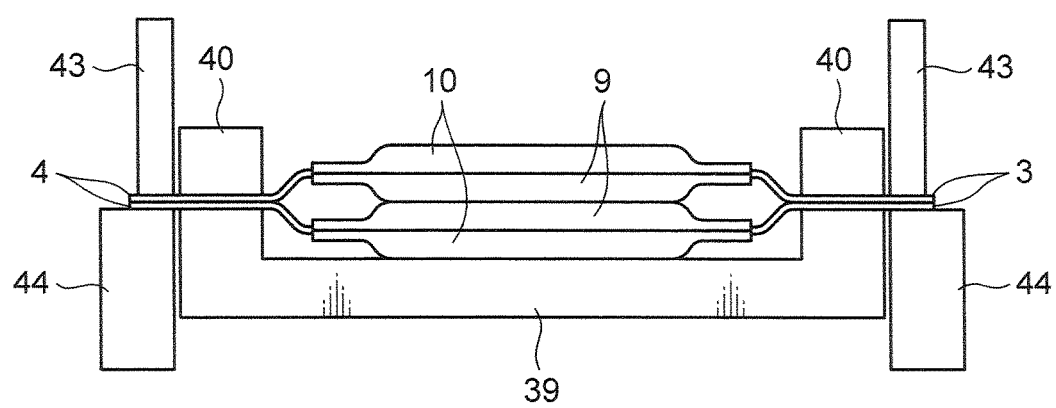
FIG. 18 is a schematic diagram illustrating a state in which side panel segments are side-sealed by a side sealing section.

FIG. 18 is a schematic diagram illustrating a state in which the side panel segment pairs 3, 4 are side-sealed by the side sealing section 41.

Referring to FIGS. 8 and 18, the side sealing section 41 comprises sealing means 43 for welding together each of the side panel segment pairs 3, 4, and an opposed roller 44 disposed in opposed relation to the sealing means 43. For example, as the sealing means 43, it is possible to employ a horn for ultrasonic-welding each of the side panel segment pairs 3, 4. The sealing means 43 and the opposed roller 44 are arranged to clamp each of the side panel segment pairs 3, 4 in the side sealing region E1. Thus, the side sealed areas 5, 6 are formed along the respective lateral edge portions of the side panel segment pairs 3, 4 (a permanently joining step). Then, the disposable diaper 1A formed with the side sealed areas 5, 6 is transferred to the third conveyer 42.

As described above, according to the first embodiment, it becomes possible to accurately fold the main body 2 in half while suppressing damage to the main body 2, and maintain a folded position of the main body 2 after the half-folding step.

More specifically, in the first embodiment, the main body 2 can be folded in half by closing the first suction-holding section 34*a* and the second suction-holding section 34*b* in a state in which the forward surface and the rearward surface of the main body 2 located on both sides of a folding line are suction-held by the suction-holding sections 34*a*, 34*b*, respectively. Thus, differently from the case where a half-folding operation is performed by pressing a tucker bar against only a portion corresponding to a folding line as in the conventional technique, the production method according to the first embodiment can fold the main body 2 in half while holding two regions to be half-folded. This makes it possible to accurately fold the main body 2 in half while suppressing damage to the main body 2. Further, in the production method, the superimposed portions of the half-folded developed module 1Z are releasably joined together. Thus, the temporarily joined areas 7, 8 allow a folded state of the main body 2 after the half-folding step to be maintained. The temporarily joined areas 7, 8 are releasable, so that a wearer can wear the wearing article by releasing the joined state of the temporarily joined areas 7, 8.

In the first embodiment, each of the temporarily joined areas 7, 8 can be formed by compressing the superimposed portions of the developed module 1Z between the protruding element 38*a* (38*b*2) and the counterpart suction-holding section. Thus, the temporarily joined areas can be formed in conjunction with the operation of folding the developed module 1Z in half. This makes it possible to more reliably maintain the folded state of the main body 2 after the half-folding step.

In the first embodiment, each of the temporarily joined areas 7, 8 can be formed in conjunction with the half-folding operation for the main body 2, by closing the suction-holding sections 34*a*, 34*b* at least one of which is formed with the protrusion element 38*a* (38*b*2). However, in the present invention, a mechanism for forming the temporarily joined areas 7, 8 is not limited to the suction-holding sections 34*a*, 34*b*. For example, a mechanism for forming the temporarily joined areas 7, 8 may be provided separately from the suction-holding sections 34*a*, 34*b*, to form the temporarily joined areas 7, 8 just after the half-folding step using the suction-holding sections 34*a*, 34*b*.

In the first embodiment, the protruding element 38*a* (38*b*2) is so configured as to be able to adjust an amount of protrusion thereof. Thus, a pressing force to be applied to the developed module 1Z can be adjusted.

In the first embodiment, the suction-holding section 34*b* has the recess 38*b* capable of allowing the protruding element 38*a* to be engaged thereinto while interposing the superimposed portions of the developed module 1Z therebetween. Thus, the superimposed portions of the developed module 1Z can be compressed not only between the distal edge face of the protruding element 38*a* and the bottom surface of the recess 38*b* but also between the outer peripheral surface of the protruding element 38*a* and the inner peripheral surface of the recess 38*b*. This makes it possible to more reliably form the temporarily joined areas 7, 8.

In the first embodiment, the temporarily joined areas 7, 8 are formed in the side panel segments 3, 4 closer to the side sealed areas 5, 6 than the main body 2. This makes it possible to more reliably maintain each of the side panel segments 3, 4 in a positional relationship set for forming the side sealed area during the side sealing operation, i.e., in a positional relationship of the superimposed portions obtained when the main body 2 is property folded in half.

In the first embodiment, during conveyance from the suction-holding sections 34*a*, 34*b* to the side sealing section 41, the developed module 1Z can be conveyed while being kept in a half-folded state. Thus, it becomes possible to reliably maintain the half-folded state of the developed module even if the developed module receives vibration or the like during conveyance.

Figure 19:
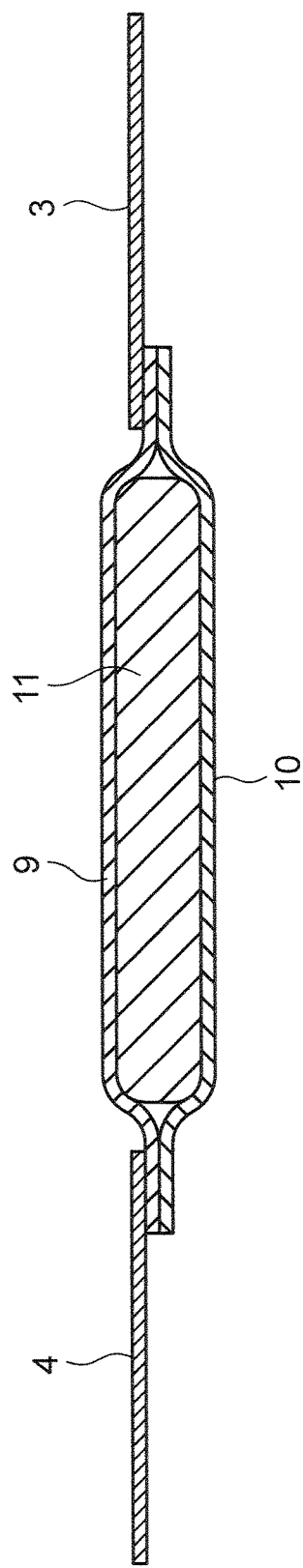
FIG. 19 a sectional view corresponding to FIG. 3, which illustrates an example of modification of the disposable diaper in FIG. 1.

The first embodiment has been described based on the disposable diaper 1A in which each of the side panel segments 3, 4 is sandwiched between the inner sheet 9 and the outer sheet 10, as illustrated in FIG. 3. Alternatively, each of the side panel segments 3, 4 may be joined onto the inner sheet 9, as illustrated in FIG. 19. In this case, the order of the Step S5 and the Step S6 may be reversed.

Figure 22:
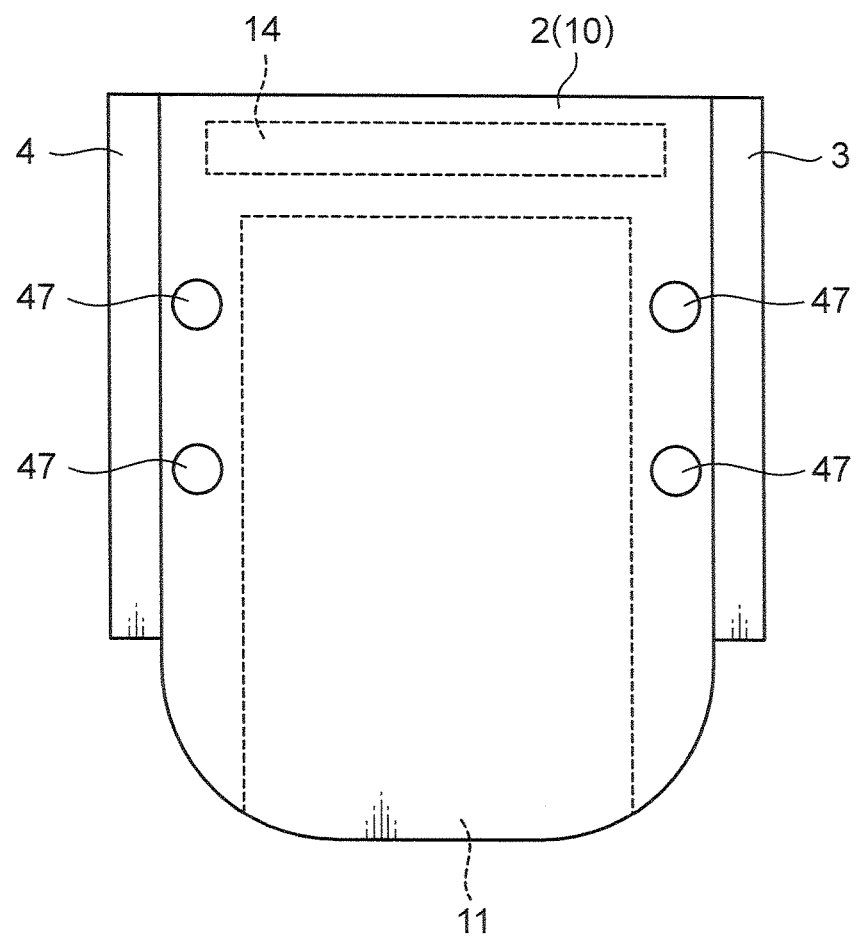
FIG. 22 is a front view illustrating a packaged state of the disposable diaper in FIG. 20.

FIG. 20 is a development diagram illustrating a general configuration of a disposable diaper 1B according to a second embodiment of the present invention. FIG. 21 is a front view illustrating a state of the disposable diaper in FIG. 20 when it is worn by a wearer. FIG. 22 is a front view illustrating a state of the disposable diaper in FIG. 20 when it is packaged. A difference from the disposable diaper 1A according to the first embodiment will be described below.

Referring to FIGS. 20 to 22, the disposable diaper 1B is different from the first embodiment in that each of a pair of side panel segments 3, 3 and a pair of side panel segments 4, 4 are not joined together. Further, the disposable diaper 1B is different from the first embodiment in that it comprises two detachable members 45, 46 each provided on a respective one of the upper (in FIG. 20) side panel segment 3 and the upper (in FIG. 20) side panel segment 4.

The detachable member 45 protrudes rightwardly (in FIG. 20) from the side panel 3. On the other hand, the detachable member 46 protrudes leftwardly (in FIG. 20) from the side panel 4. Each of the detachable members 45, 46 is a sheet having a detachable surface (surface facing a front side in FIG. 20) detachably attachable with respect to an outer surface (outer sheet 10) of the main body 2. Specifically, as each of the detachable members 45, 46, it is possible to employ an adhesive tape or a mechanical fastener (hook and loop fastener), for example. When a mechanical fastener is used as each of the detachable members 45, 46, it is necessary to use a hook member and a loop member in a paired manner. In the second embodiment, a nonwoven sheet is employed as the outer sheet 10 of the main body 2. Thus, a hook member may be employed as each of the detachable members 45, 46, and the nonwoven sheet may be utilized as a loop member. Alternatively, a loop member may be additionally provided on the outer sheet 10.

When a wearer wears the disposable diaper 1B, after the main body 2 is disposed to extend from a front abdominal region to a rear dorsal region via a crotch region of the wearer, the side panel segments 3, 4 each provided with a respective one of the detachable members 45, 46 are positioned to extend in a front-rear direction to cover a lateral surface of a waist region of the wearer, and the detachable members 45, 46 are fixed onto the outer surface of the main body 2, as illustrated in FIG. 21. In this manner, the disposable diaper 1B can be worn while covering the lateral surface of the waist region of the wearer by the side panel segments 3, 3, 4, 4.

When the disposable diaper 1B is packaged in a packaging material as a finished product, the disposable diaper 1B in a developed state illustrated in FIG. 20 is folded into a state illustrated in FIG. 22. More specifically, each of the side panel segments 3, 4 is folded back toward the main body 2 in such a manner that the detachable surface of each of the detachable members 45, 46 faces toward the inner sheet 9, and the main body 2 is folded in half in such a manner that each of the fold-back side panel segments 3, 4 is located inside. The disposable diaper 1B in the packaged state has four temporarily joined areas 47 each releasably joining superimposed portions of the main body 2 together. Thus, the temporarily joined areas 47 allow a half-folded state of the main body 2 to be maintained, so that it becomes possible to reliably maintain a half-folded packaged state of the disposable diaper 1B.

Figure 23:
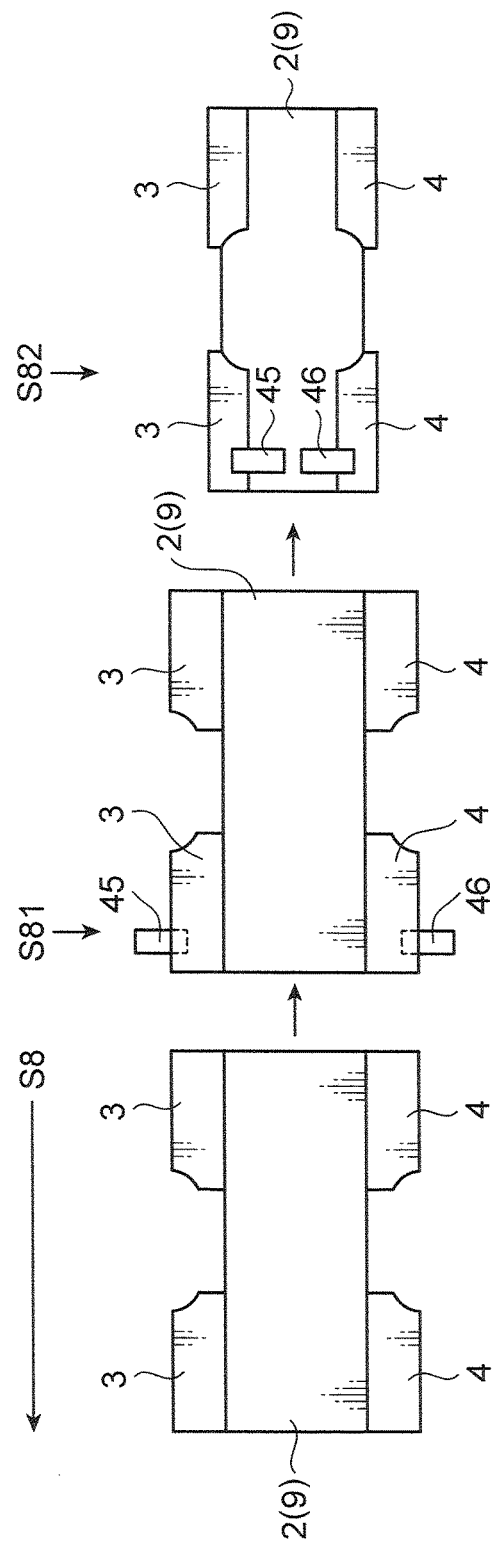
FIG. 23 is a process chart corresponding to FIG. 7, which illustrates a production process for the disposable diaper in FIG. 20.

With reference to FIG. 23, a production method for the disposable diaper 1B will be described below.

FIG. 23 is a process chart corresponding to FIG. 7, which illustrates a production process for the disposable diaper 1B in FIG. 20.

The production method for the disposable diaper 1B comprises Steps S1 to S8 which are identical to the aforementioned Steps S1 to S8 (see FIG. 6) in the first embodiment. Subsequently to the Step S8, the following Steps S81 and S82 are performed.

<Step S81>

In Step S81, the detachable members 45, 46 are joined to the side panel segment 3 and the side panel segment 4, respectively.

<Step S82>

In Step S82, each of the side panel segments 3, 3, 4, 4 is folded back toward the main body 2 in such a manner that the detachable surface (surface facing a front side in FIG. 20) of each of the detachable members 45, 46 faces toward the inner sheet 9 of the main body 2.

Then, after completion of the Step S82, the main body 2 is folded in half using the folding unit 22, and superimposed portions of the main body 2 are releasably joined together to form the temporarily joined areas 47. In this embodiment, each of the temporarily joined areas 47 is formed at a position offset from the absorbent body 11, the detachable members 45, 46 and the elastic members 12, 14.

In FIG. 22, the point of forming the temporarily joined area 47 in the superimposed portions of the main body 2 has been described. However, the temporarily joined area 47 may be formed in superimposed portions of the side panel segments 3, 3, 4, 4 (superimposed portions of four sheets).

In FIGS. 20 to 23, the disposable diaper 1B having the side panel segments 3, 3, 4, 4 formed in respective longitudinally opposite end portions of the main body 2. Alternatively, the remaining side panel segments 3, 4 other than the side panel segments 3, 4 each provided with a respective one of the detachable members 45, 46 may be omitted. That is, the disposable diaper may be configured to cover a lateral surface of a waist region of a wearer by only a pair of right and left side panel segments 3, 4.

As described above, according to the second embodiment, the disposable diaper 1B can be produced which is capable of being worn by: positioning the main body 2 to extend from a front abdominal region to a rear dorsal region via a crotch region of a wearer; positioning the side panel segments 3, 3, 4, 4 to extend in a front-rear direction to cover a lateral surface of a waist region of the wearer; and fixing the detachable members 45, 46 onto the outer surface of the main body 2.

Figure 24:
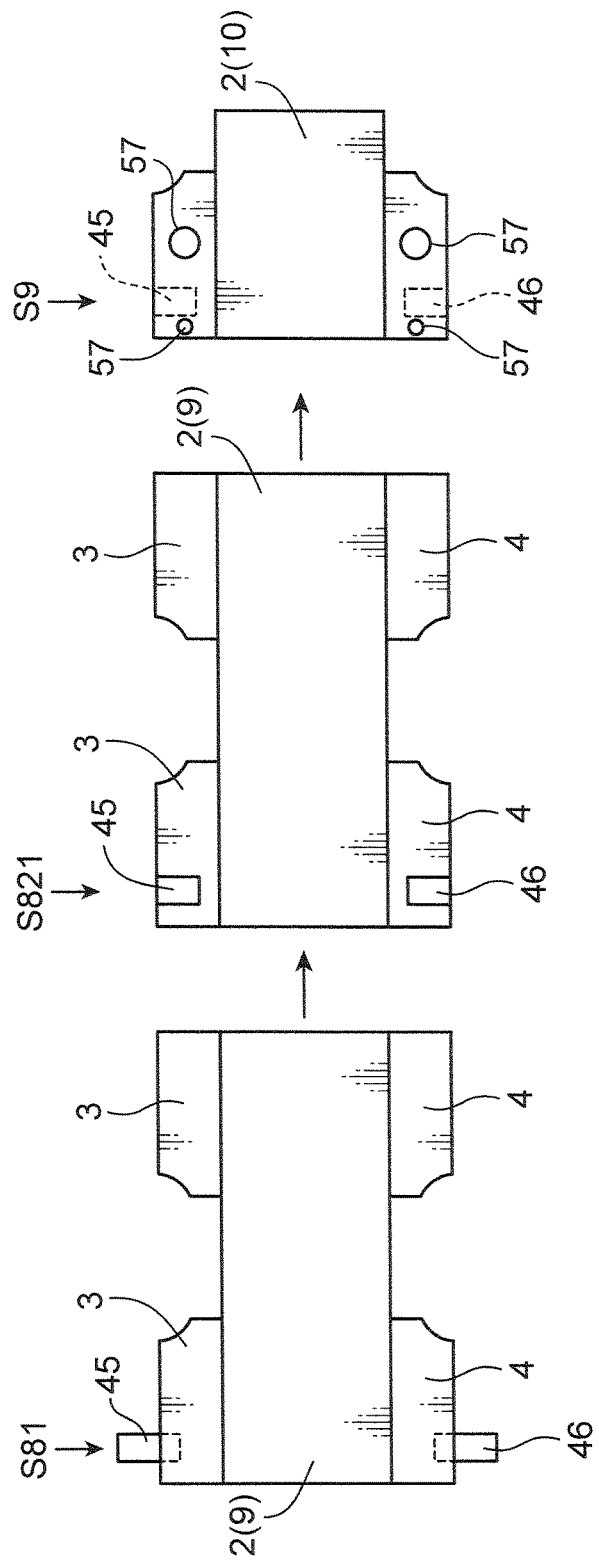
FIG. 24 is a process chart illustrating an example of modification of the disposable diaper production process in FIG. 23.

In the second embodiment, in the Step S82, each of the side panel segments 3, 3, 4, 4 is folded back toward the main body 2. Alternatively, as illustrated in FIG. 24, each of the detachable members 45, 46 may be folded back toward the main body 2. FIG. 24 is a process chart illustrating an example of modification of the disposable diaper production process in FIG. 23.

In this modified production method, after joining the each of the detachable members 45, 46 in the Step S81, the following Step S821 is performed, instead of the Step S82.

<Step S821>

In Step S821, each of the detachable members 45, 46 is folded back toward the main body 2 in such a manner that the detachable surface (surface facing a front side in FIG. 24) of each of the detachable members 45, 46 faces toward the inner sheet 9 of the main body 2.

Then, after completion of the Step S821, the main body 2 is folded in half in the Step S9 using the folding unit 22, and resulting superimposed portions of a respective pair of the side panel segments 3, 3, 4, 4 are releasably joined together to form a temporarily joined area 57. In this case, each of the temporarily joined areas 47 is formed at a position offset from a respective one of the detachable members 45, 46.

In the second embodiment, in the Step S82 or S821, each of the side panel segments 3, 3, 4, 4 or each of the detachable members 45, 46 is folded back toward the main body 2. Alternatively, superimposed portions of the side panel segments 3, 3, 4, 4 and the detachable members 45, 46 may be folded back. In this case, the detachable surface of each of the detachable members 45, 46 can be positioned to face toward the inner sheet 9 of the main body 2.

Figure 25:
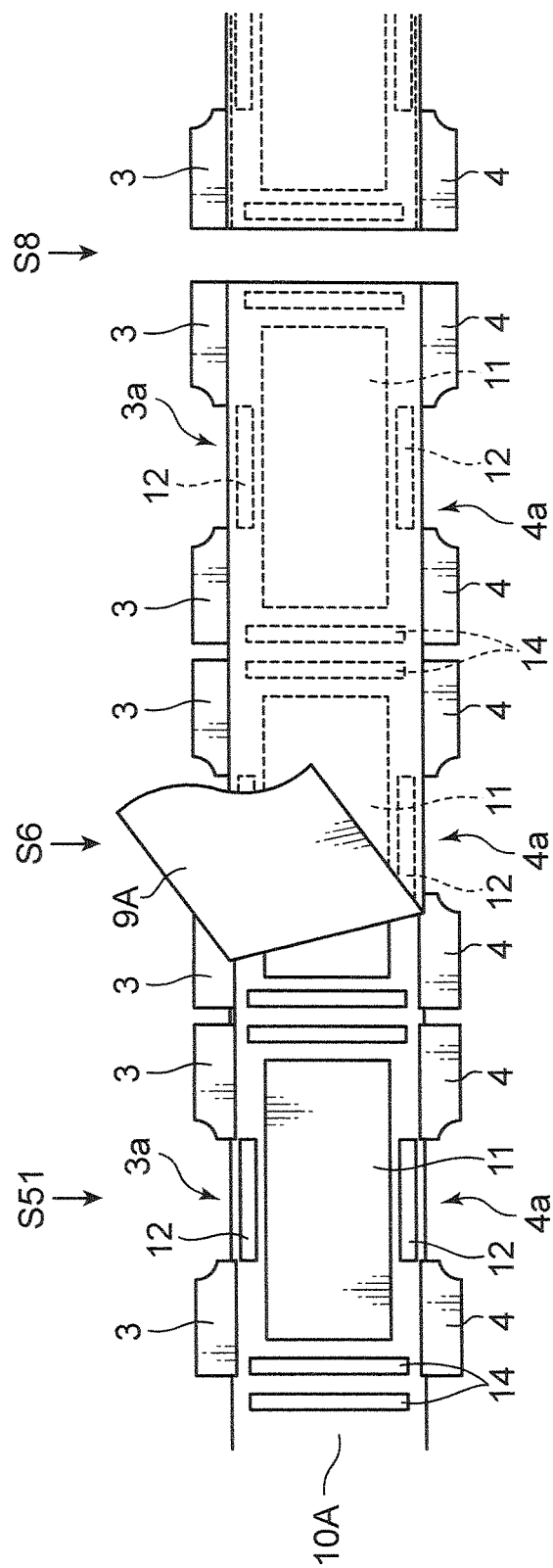
FIG. 25 is a process chart of a disposable diaper production method according to a third embodiment of the present invention.
Figure 26:
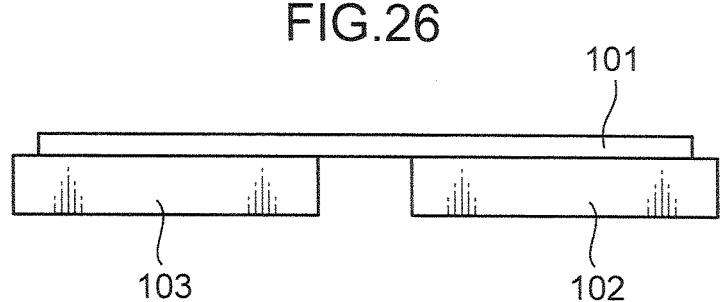
FIG. 26 is a schematic diagram of a folding operation using a folding apparatus of the Patent Document 2.
Figure 27:
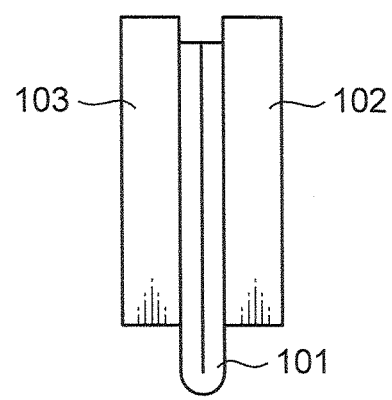
FIG. 27 is a schematic diagram of the folding operation using the folding apparatus of the Patent Document 2.
Figure 28:
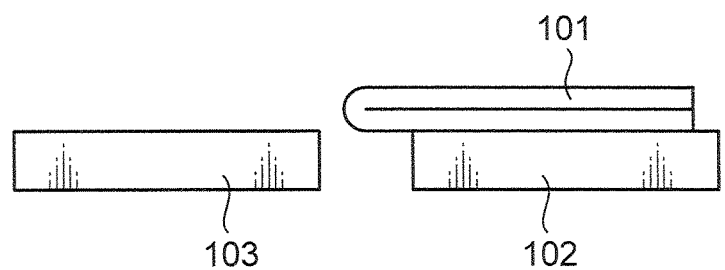
FIG. 28 is a schematic diagram of the folding operation using the folding apparatus of the Patent Document 2.

In the first and second embodiments, as illustrated in FIG. 6, the side panel segments 3, 4 are formed by cutting the side panel strips 3A, 4A joined onto the outer sheet strip 10A. Alternatively, as illustrated in FIG. 25, side panel segments 3, 4 each cut into a predetermined size may be joined to the outer sheet strip 10A. FIG. 25 is a process chart of a disposable diaper production method according to a third embodiment of the present invention.

In the embodiment illustrated in FIG. 25, the following Step S51 is performed, instead of the Step S5.

<Step S51>

In Step S51, the side panel strips 3A, 4A are cut into individual side panel segments 3, 4, and the resulting side panel segments 3, 4 are joined onto the outer sheet strip 10A. In this case, the pair of side panel segments 3, 3, 4, 4 are disposed at positions corresponding to longitudinally opposite ends of the absorbent body 11, at intervals of a distance equivalent to the leg-hole space 3a, 4a. Further, a distance between the side panel segments 3, 3, 4, 4 located between adjacent two of the spaces 3a, 4a is set to allow the cutting blade to pass through therebetween in the subsequent Step S8.

According to the production method illustrated in FIG. 25, differently from the first and second embodiments, the Step S7 (see FIG. 6) for forming the leg-hole spaces 3a, 4a can be omitted.

Although, in the Step S51 illustrated in FIG. 25, the side panel strips 3A, 4A are cut into individual side panel segments 3, 3, 4, 4, the present invention is not limited thereto. For example, in the Step S51, a first strip having a length of two side panel segments 3 and a second strip having a length of two side panel segments 4 may be subjected to the joining. In this case, the first and second strips are arranged at intervals of a distance equivalent to the leg-hole space 3a, 4a, and cut into two side panel segments 3, 3, 4, 4 in the subsequent Step S8. This makes it possible to halve the number of components to be subjected to the joining in the Step S51, thereby enhancing efficiency of the operation in the Step S51.

Although the above embodiments have been described based on the disposable diapers 1A, 1B having the absorbent body 11, the temporarily joined areas 7, 8, 47 may be formed in a wearing article devoid of the absorbent body 11. In this case, the Step S3 for joining absorbent body 11 may be omitted from the production method according to each of the above embodiments.

The above specific embodiments primarily include inventions having the following features.

In order to solve the aforementioned problems, the present invention provides a method for producing a wearing article which comprises a main body adapted to extend from a front abdominal region to a rear dorsal region via a crotch region of a wearer, and a side panel for covering a lateral surface of a waist region of the wearer. The method comprises: an developed module preparing step of preparing an developed module which comprises the main body, and at least two side panel segments extending from at least one of front and rear end portions of the main body, laterally in respective opposite directions; a suction-holding section preparing step of preparing a first suction-holding section having a first suction-holding surface capable of suction-holding a forward surface of the main body in the developed module, and a second suction-holding section having a second suction-holding surface capable of suction-holding a rearward surface of the main body in the developed module; a suction-holding section positioning step of positioning the first suction-holding section and the second suction-holding section in such a manner that the first suction-holding surface and the second suction-holding surface are aligned side-by-side while facing a same side; a suction-holding step of, after the suction-holding section positioning step, suction-holding the forward surface of the main body in the developed module by the first suction-holding surface, and suction-holding the rearward surface of the main body in the developed module by the second suction-holding surface; a half-folding step of, after the suction-holding step, closing the first suction-holding section and the second suction-holding section in such a manner that the first suction-holding surface and the second suction-holding surface face each other, thereby folding the main body in half; and a temporarily joining step of externally heating and/or pressing superimposed portions of the developed module half-folded by the half-folding step, thereby releasably joining the superimposed portions of the developed module.

The present invention further provides an apparatus for producing a wearing article using an developed module which comprises a main body, and at least two side panel segments extending from at least one of front and rear end portions of the main body, laterally in respective opposite directions, wherein the wearing article is capable of being worn in a state in which the main body extends from a front abdominal region to a rear dorsal region via a crotch region of a wearer, and the side panel segments cover a lateral surface of a waist region of the wearer. The apparatus comprises: a first suction-holding section having a first suction-holding surface capable of suction-holding a forward surface of the main body in the developed module; a second suction-holding section having a second suction-holding surface capable of suction-holding a rearward surface of the main body in the developed module; a support member supporting the first suction-holding section and the second suction-holding section in such a manner that the suction-holding sections are relatively displaceable between an open position where the first suction-holding surface and the second suction-holding surface are aligned side-by-side while facing a same side, and a closed position where the first suction-holding surface and the second suction-holding surface face each other; and a temporarily joining portion provided in at least one of the first suction-holding section and the second suction-holding section, and adapted to externally heat and/or press superimposed portions of the developed module half-folded between the first and second suction-holding surfaces at the closed position, thereby releasably joining the superimposed portions together.

In the above method and apparatus of the present invention, it is possible to accurately fold the main body in half while suppressing damage to the main body, and maintain a folded position of the main body after the half-folding step.

More specifically, in the present invention, the main body can be folded in half by closing the first suction-holding section and the second suction-holding section in a state in which the forward surface and the rearward surface of the main body located on both sides of a folding line are suction-held by the two suction-holding sections, respectively. Thus, differently from the case where a half-folding operation is performed by pressing a tucker bar against only a portion corresponding to a folding line as in the conventional technique, the main body can be folded in half while holding two regions (the forward surface and the rearward surface of the main body) to be half-folded, so that it is possible to accurately fold the main body in half while suppressing damage to the main body. Further, in the production method of the present invention, the superimposed portions of the half-folded developed module are releasably joined together. Thus, the temporarily joined area allows a folded state of the main body after the half-folding step to be maintained. The temporarily joined area is releasable, so that a wearer can wear the wearing article by releasing the joined state of the temporarily joined area.

As compared to the case where the developed module is superimposedly joined using an adhesive, the production method of the present invention designed to externally heat and/or press the developed module, thereby temporarily joining the superimposed portions of the developed module, has the following advantageous effects. In the case of using an adhesive, it is necessary to prepare not only the adhesive as consumable supply but also a facility for applying the adhesive. As a result, a product cost of the wearing article is increased. In contrast, the production method of the present invention can suppress a product cost of the wearing article. Moreover in the case of using an adhesive, the applied adhesive is likely to adhere to a production facility and others, causing deterioration in production efficiency. In contrast, the production method of the present invention can avoid such deterioration in production efficiency. Further, in the case of using an adhesive, air permeability of the main body or the side panel is likely to be impaired in a region applied with the adhesive, and skin problems are likely to occur due to contact with the adhesive, depending on wearer's constitution. In contrast, the production method of the present invention can suppress such problems.

As used here, the term "side panel" means a component of a wearing article during use or wearing, wherein opposite ends of the component are coupled to the main body to cover a lateral surface of a waist region of a wearer. The term "side panel segment" means a member constituting the side panel and having at least one end separated from the main body.

Preferably, in the production method of the present invention, in the temporarily joining step, a temporarily joining portion provided in at least one of the first suction-holding section and the second suction-holding section is brought into contact with the superimposed portions of the developed module during a period of performing the half-folding step, thereby releasably joining the superimposed portions of the developed module.

In this method, the temporarily joined area can be formed during the period of performing the half-folding step by the temporarily joining portion provided in at least one of the first and second suction-holding sections. Thus, as compared to the case where the temporarily joining step is performed after the half-folding step, an operation time can be shortened.

Preferably, in the above production method, the temporarily joining portion comprises a protruding element protruding from at least one of the first suction-holding surface and the second suction-holding surface, wherein, in the temporarily joining step, the superimposed portions of the developed module are compressed between the protruding element and the counterpart suction-holding section.

Preferably, in the production apparatus of the present invention, the temporarily joining portion comprises a protruding element protruding from at least one of the first suction-holding surface and the second suction-holding surface, and adapted to compress the superimposed portions of the developed module in cooperation with the counterpart suction-holding section.

In these production method and production apparatus, the temporarily joined area can be formed by compressing the superimposed portions of the developed module between the protruding element and the counterpart suction-holding section. Thus, the temporarily joined area can be formed in conjunction with the operation of folding the developed module in half, so that it is possible to more reliably maintain the folded state of the main body after the half-folding step.

Preferably, in the above production apparatus, the protruding element is so configured as to be able to adjust an amount of protrusion of the protruding element from at least one of the first suction-holding surface and the second suction-holding surface.

In this production apparatus, a joining level of the temporarily joined area can be adjusted by adjusting an amount of protrusion of the protruding element to adjust a pressing force to be applied to the developed module.

Preferably, in the above production method, the temporarily joining portion further comprises a recess formed in a counterpart one of the first suction-holding surface and the second suction-holding surface, with respect to the protruding element, wherein, in the temporarily joining step, the protruding element is engaged into the recess while interposing the superimposed portions of the developed module therebetween, thereby compressing the superimposed portions of the developed module.

Preferably, in the above production apparatus, the temporarily joining portion further comprises a recess formed in a counterpart one of the first suction-holding surface and the second suction-holding surface, with respect to the protruding element, and configured in such a manner that the protruding element can be engaged into the recess while interposing the superimposed portions of the developed module therebetween.

In these production method and production apparatus, the superimposed portions of the developed module can be compressed not only between a distal edge face of the protruding element and a bottom surface of the recess but also between an outer peripheral surface of the protruding element and an inner peripheral surface of the recess. This makes it possible to more reliably form the temporarily joined area.

Preferably, in the production method of the present invention, in the developed module preparing step, the developed module is prepared, the developed module comprising four side panel segments a respective two of which extend from a respective one of the front and rear end portions of the main body, laterally in respective opposite directions, wherein, in the suction-holding section preparing step, a suction-holding surface capable of suction-holding two of the side panel segments extending from the front end portion of the main body in the developed module, laterally in respectively opposite directions, is prepared as the first suction-holding surface, and a suction-holding surface capable of suction-holding two side panel segments extending from the rear end portion of the main body in the developed module, laterally in respective opposite directions, is prepared as the second suction-holding surface, and wherein the method further comprises a permanently joining step of, after the temporarily joining step, joining together lateral edge portions of a respective pair of the side panel segments superimposed by the half-folding step.

Preferably, in the production apparatus of the present invention, the developed module comprises four side panel segments a respective two of which extend from a respective one of the front and rear end portions of the main body, laterally in respective opposite directions, wherein the first suction-holding surface is capable of suction-holding two of the side panel segments extending from the front end portion of the main body in the developed module, laterally in respective opposite directions, wherein the second suction-holding surface is capable of suction-holding two side panel segments extending from the rear end portion of the main body of the developed module, laterally in respective opposite directions, and wherein the apparatus further comprises a permanently joining section for joining together lateral edge portions of a respective pair of the side panel segments superimposed in the developed module half-folded by the first and second suction-holding sections.

In these production method and production apparatus, by using the developed module comprising four side panel segments a respective two of which extend from a respective one of the front and rear end portions of the main body, laterally in respective opposite directions, a pant-type wearing article can be produced by joining together lateral edge portions of the pair of side panel segments superimposed when the main body is folded in half.

Preferably, in the above production method, in the temporarily joining step, the respective pair of side panel segments superimposed by the half-folding step is releasably joined.

Preferably, in the above production apparatus, the temporarily joining portion is adapted to releasably join the respective pair of side panel segments superimposed between the first and second suction-holding sections.

In these production method and production apparatus, the side panel segment pair closer to a permanently joined area than the main body is joined. This makes it possible to more reliably maintain the side panel segment pair in a positional relationship set for permanent joining, i.e., in a positional relationship of the superimposed portions obtained when the main body is property folded in half.

Preferably, the above production method further comprises: an opening step of, after the temporarily joining step, opening the first and second suction-holding sections; and a conveying step of, after the opening step, conveying the half-folded developed module from the first and second suction-holding sections to a position where the permanently joining step is performed, wherein, in the conveying step, the half-folded developed module is conveyed while being kept in a half-folded state by being clamped in a superimposing direction thereof.

Preferably, the above production apparatus further comprises a conveying section capable of receiving the half-folded developed module from the first and second suction-holding sections moved to the open position, and conveying the received developed module to the permanently joining section, wherein the conveying section is adapted to convey the developed module while keeping the developed module in a half-folded state.

In these production method and production apparatus, during conveyance from the suction-holding sections to the position where the permanently joining step is performed (permanently joining section), the developed module can be conveyed while being kept in the half-folded state. Thus, it is possible to reliably maintain the half-folded state of the developed module even if the developed module receives vibration or the like during conveyance.

Preferably, in the above production method, the developed module is conveyed while at least a portion of the superimposed side panel segments is clamped, in the conveying step.

Preferably, in the above production apparatus, the conveying section comprises a first conveyer for conveying the developed module while holding the developed module from therebelow, and a second conveyer for conveying the developed module while clamping at least a portion of the superimposed side panel segments in cooperation with the first conveyer.

In these production method and production apparatus, the developed module can be conveyed while the side panel segment pair located closer to a permanently joined area than the main body is clamped. This makes it possible to more reliably maintain the side panel segment pair in a positional relationship set for permanent joining, during the period of performing the permanently joining step.

Preferably, the production method of the present invention further comprises: an attaching step of attaching at least two detachable members to respective ones of the side panel segments, each of the detachable members having a detachable surface detachably attachable with respect to an outer surface of the main body; and a fold-back step of, prior to the half-folding step, folding back at least one of the side panel segments and the detachable members, onto the main body, in such a manner that the detachable surfaces of the detachable members faces toward an inner surface of the main body, wherein, in the half-folding step, the main body is folded in half in such a manner that the folded-back side panel segments are located inside.

In this method, a wearing article can be produced which is capable of being worn by: positioning the main body to extend from a front abdominal region to a rear dorsal region via a crotch region of a wearer; positioning the side panel segments extending laterally from the main body to extend in a front-rear direction to cover a lateral surface of a waist region of the wearer; and fixing the detachable members onto the outer surface of the main body.

The present invention further provides a wearing article produced by the above production method.

The present invention further provides a wearing article including an developed module which comprises a main body and at least two side panel segments extending from at least one of front and rear end portions of the main body, laterally in respectively opposite directions, wherein the main body is folded in half, the wearing article comprising a temporarily jointed area where superimposed portions of the developed module are releasably joined together.

The wearing article of the present invention can be obtained through a production method capable of accurately folding the main body in half while suppressing damage to the main body, and maintaining a folded position of the main body after the half-folding step.

More specifically, the wearing article of the present invention can be obtained through a production method capable of folding the main body in half by closing the first suction-holding section and the second suction-holding section in a state in which the forward surface and the rearward surface of the main body located on both sides of a folding line are suction-held by the suction-holding sections, respectively. Thus, in the wearing article of the present invention, a production method may be employed which is designed to fold the main body in half while holding two regions (the forward surface and the rearward surface of the main body) to be half-folded, differently from the case where a half-folding operation is performed by pressing a tucker bar against only a portion corresponding to a folding line as in the conventional technique. This makes it possible to accurately fold the main body in half while suppressing damage to the main body. Further, in the wearing article of the present invention, the superimposed portions of the half-folded developed module are releasably joined together. Thus, a folded state of the main body after the half-folding step can be maintained. Further, the temporarily joined area is releasable, so that a wearer can wear the wearing article by releasing the joined state of the temporarily joined area.

Preferably, in the above wearing article, the developed module has four side panel segments a respective two of which extend from a respective one of the front and rear end portions of the main body, laterally in respective opposite directions, wherein the wearing article further comprises a permanently joined area formed by joining together lateral edge portions of a respective pair of the side panel segments superimposed in a state in which the main body is folded in half, and wherein the temporarily joined area is formed by releasably joining the side panel segments superimposed in a state in which the main body is folded in half, at a position other than that of the permanently joined area.

In this wearing article, the temporarily joined area is formed at a position other than that of the permanently joined area. Thus, in comparison between this wearing article and other wearing article, whether or not a wearing article is a type formed by permanently joining side panel segments together in a state in which the side panel segments are accurately positioned can be readily determined by checking a presence or absence of the temporarily joined area.

The present invention makes it possible to accurately fold the main body in half while suppressing damage to the main body, and maintain a folded position of the main body after the half-folding step.

What is claimed is:

1. A method for producing a wearing article that comprises a main body adapted to extend from a front abdominal region to a rear dorsal region via a crotch region of a wearer, and a side panel for covering a lateral surface of a waist region of the wearer, comprising:
    a developed module preparing step of preparing a developed module that comprises the main body, and at least two side panel segments extending from at least one of front and rear end portions of the main body, laterally in respective opposite directions;
    a suction-holding section preparing step of preparing a first suction-holding section having a first suction-holding surface capable of suction-holding a forward surface of the main body in the developed module, and a second suction-holding section having a second suction-holding surface capable of suction-holding a rearward surface of the main body in the developed module;
    a suction-holding section positioning step of positioning the first suction-holding section and the second suction-holding section in such a manner that the first suction-holding surface and the second suction-holding surface are aligned side-by-side while facing a same side;
    a suction-holding step of, after the suction-holding section positioning step, suction-holding the forward surface of the main body in the developed module by the first suction-holding surface, and suction-holding the rearward surface of the main body in the developed module by the second suction-holding surface;
    a half-folding step of, after the suction-holding step, closing the first suction-holding section and the second suction-holding section in such a manner that the first suction-holding surface and the second suction-holding surface face each other, thereby folding the main body in half; and
    a temporarily joining step of externally heating and/or pressing superimposed portions of the developed module half-folded by the half-folding step, thereby releasably joining the superimposed portions of the developed module, wherein
    in the temporarily joining step, a temporarily joining portion provided in at least one of the first suction-holding section and the second suction-holding section is brought into contact with the superimposed portions of the developed module during a period of performing the half-folding step, thereby releasably joining the superimposed portions of the developed module,
    the temporarily joining portion comprises a protruding element protruding from at least one of the first suction-holding surface and the second suction-holding surface, the protruding element including a distal end surface parallel to the at least one of the first suction-holding surface and the second suction-holding surface,
    a counterpart suction-holding section other than one suction-holding section includes a surface parallel to a counterpart suction-holding surface of the counterpart suction-holding section among the first suction-holding surface and the second suction-holding surface, the one suction-holding section being a suction-holding section provided with the protruded element among the first suction-holding section and the second suction-holding section,
    in the suction-holding section positioning step, the first suction-holding section and the second suction-holding section are positioned in such a manner that the distal end surface of the protruding element and the surface of the counterpart suction-holding section face a same side,
    in the half folding step, the first suction-holding section and the second suction-holding section are closed in such a manner that the distal end surface of the protruding element and the surface of the counterpart suction-holding section face each other, and
    in the temporarily joining step, the superimposed portions of the developed module are compressed between the distal end surface of the protruding element and the surface of the counterpart suction-holding section by closing the first suction-holding section and the second suction holding section in the half-folding step, thereby the main body is folded in half while releasably joining the superimposed portions of the developed module.

2. The method for producing a wearing article according to claim 1,
wherein the temporarily joining portion further comprises a recess formed in the counterpart suction-holding surface of the counterpart suction-holding section, and
wherein, in the temporarily joining step, the protruding element is engaged into the recess while interposing the superimposed portions of the developed module therebetween, thereby compressing the superimposed portions of the developed module.

3. The method for producing a wearing article according to claim 1,
wherein, in the developed module preparing step, the developed module is prepared, the developed module comprising four side panel segments a respective two of which extend from a respective one of the front and rear end portions of the main body, laterally in respective opposite directions,
wherein, in the suction-holding section preparing step, a suction-holding surface capable of suction-holding two of the side panel segments extending from the front end portion of the main body in the developed module, laterally in respectively opposite directions, is prepared as the first suction-holding surface, and a suction-holding surface capable of suction-holding two side panel segments extending from the rear end portion of the main body in the developed module, laterally in respective opposite directions, is prepared as the second suction-holding surface, and
wherein the method further comprises a permanently joining step of, after the temporarily joining step, joining together lateral edge portions of a respective pair of the side panel segments superimposed by the half-folding step.

4. The method for producing a wearing article according to claim 3, wherein, in the temporarily joining step, the respective pair of side panel segments superimposed by the half-folding step is releasably joined.

5. The method for producing a wearing article according to claim 3, further comprising:
an opening step of, after the temporarily joining step, opening the first and second suction-holding sections; and
a conveying step of, after the opening step, conveying the half-folded developed module from the first and second suction-holding sections to a position where the permanently joining step is performed,
wherein, in the conveying step, the half-folded developed module is conveyed while being kept in a half-folded state by being clamped in a superimposing direction thereof.

6. The method for producing a wearing article according to claim 5, wherein, in the conveying step, the developed module is conveyed while at least a portion of the superimposed side panel segments is clamped.

7. The method for producing a wearing article according to claim 1, further comprising:
an attaching step of attaching at least two detachable members to respective ones of the side panel segments, each of the detachable members having a detachable surface detachably attachable with respect to an outer surface of the main, body; and
a fold-back step of, prior to the half-folding step, folding back at least one of the side panel segments and the detachable members, onto the main body, in such a manner that the detachable surfaces of the detachable members faces toward an inner surface of the main body,
wherein, in the half-folding step, the main body is folded in half in such a manner that the folded-back side panel segments are located inside.

* * * * *